US011299784B2

United States Patent
Valesia et al.

(10) Patent No.: US 11,299,784 B2
(45) Date of Patent: Apr. 12, 2022

(54) BIOMARKERS FOR PREDICTING DEGREE OF WEIGHT LOSS

(71) Applicant: NESTEC S.A., Vevey (CH)

(72) Inventors: Armand Valesia, Chavannes-pres-Renens (CH); Jorg Hager, Houtaud (FR); Jerome Carayol, Pully (CH)

(73) Assignee: Societe des Produits Nestle S.A., Vevey (CH)

(*) Notice: Subject to any disclaimer, the term of this patent is extended or adjusted under 35 U.S.C. 154(b) by 204 days.

(21) Appl. No.: 16/304,758

(22) PCT Filed: May 30, 2017

(86) PCT No.: PCT/EP2017/062942
§ 371 (c)(1),
(2) Date: Nov. 27, 2018

(87) PCT Pub. No.: WO2017/207513
PCT Pub. Date: Dec. 7, 2017

(65) Prior Publication Data
US 2019/0330697 A1      Oct. 31, 2019

(30) Foreign Application Priority Data

May 31, 2016   (EP) .................................... 16172242

(51) Int. Cl.
| | | |
|---|---|---|
| *C12Q 1/68* | (2018.01) |
| *C12Q 1/6883* | (2018.01) |
| *G16H 50/30* | (2018.01) |
| *G16H 50/70* | (2018.01) |
| *G16H 50/20* | (2018.01) |
| *G16B 5/00* | (2019.01) |
| *G16B 20/20* | (2019.01) |
| *G16B 40/10* | (2019.01) |

(52) U.S. Cl.
CPC ............. *C12Q 1/6883* (2013.01); *G16B 5/00* (2019.02); *G16B 20/20* (2019.02); *G16B 40/10* (2019.02); *G16H 50/20* (2018.01); *G16H 50/30* (2018.01); *G16H 50/70* (2018.01); *C12Q 2600/156* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

2014/0057800 A1\* 2/2014 Brattbakk ............ C12Q 1/6883
506/9

FOREIGN PATENT DOCUMENTS

JP    2013528055 A    7/2013
WO    2016078944      5/2016

OTHER PUBLICATIONS

Sorensen, Thorkild et al. Genetic Polymorphisms and Weight Loss in Obesity: A Randomised Trial of Hypo-Energetic High-versus low-fat Diets (2006) PLoS Clin Trials; 1(2): e12 (Year: 2006).\*
Yoon, Yoosik et al. Effects of genetic polymorphisms of UCP2 and UCP3 on very low calorie diet-induced body fat reduction in Korean female students (2007) Biochem and Biophys Res Comm 359:451-456 (Year: 2007).\*
Ha, Misook et al. Interspecies Regulation of MicroRNAs and Their Targets (2008) Biochim Biophys Acta 1779(11): 735-742 (Year: 2008).\*
Soenen, S. et al. Relationship between perilipin gene polymorphisms and body weight and body composition during weight loss and weight maintenance (2009) Physiol Behav 96:723-728 (Year: 2009).\*
Vann, Madeline The GenoType Diet (2010) (Year: 2010).\*
Milagro, Fermin et al. High-Throughput Sequencing of microRNAs in Peripheral Blood Mononuclear Cells: Identification of Potential Weight Loss Biomarkers (2013) PLoS ONE 8(1); e54319 (Year: 2013).\*
Ortega, Franisco et al. Targeting the Circulating MicroRNA Signature of Obesity (2013) Clinical Chemistry 59:5, 781-792 (Year: 2013).\*
Wu, Honguy et al. Dietary Interventions for Weight Loss and Maintenance: Preference or Genetic Personalization (2013) Curr Nutr Rep 2:189-198 (Year: 2013).\*
Prats-Puig, Anna et al. Changes in Circulating MicroRNAs are Associated with Childhood Obesity J Clin Endocrinol Metab, Oct. 2013, 98(10):E1655-1660 (Year: 2013).\*
Flowers, Elena et al. Circulating microRNA-320a and microRNA-486 predict thiazolidinedione response: Moving towards precision health for diabetes prevention (2015) Metabolism Clinical and Experimental 64:1051-1059 (Year: 2015).\*
Flowers, Elena et al. MicroRNAs associated with exercise and diet: a systemic review (2015) Physiol Genomics 47:1-11 (Year: 2015).\*
Wang, Li-Sheng et al. MicroRNA-486 regulates normal erythropoiesis and enhances growth and modulates drug response in CML progenitors (2015) Blood, 125(8): 1302-1313 (Year: 2015).\*
Wang, Li-Sheng et al. MicroRNA-486 regulates normal erythropoiesis and enhances growth and modulates drug response in CML progenitors (2015) Blood, 125(8): 1302-1313 (Year: 2015).\*
Aller, Erik et al. Genetic Predictors of >=5% Weight Loss by Multidisciplinary Advice to Severely Obese Subjects (2017) J Nutrigenet Nutrigenomics 10:32-42 (Year: 2017).\* Tan, Pui Yee et al. Lifestyle Interventions for Weight Control Modified by Genetic Variation: A Review of the Evidence (2018) Public Health Genomics 21:169-185 (Year: 2018).\*

(Continued)

*Primary Examiner* — Jeanine A Goldberg
*Assistant Examiner* — Jennifer L. Overly
(74) *Attorney, Agent, or Firm* — K&L Gates LLP

(57) ABSTRACT

The present invention relates to a method for predicting the degree of weight loss attainable by applying one or more dietary interventions to a subject and/or the degree of maintenance of weight loss following one or more dietary interventions; which method comprises determining the level of microRNA-486 (miR-486) in one or more samples obtained from the subject; and/or determining the nucleotide of the subject at one or more polymorphic positions genetically linked to miR-486.

3 Claims, 6 Drawing Sheets

Specification includes a Sequence Listing.

(56) References Cited

OTHER PUBLICATIONS

Stein, Natalie Seven Reasons Why You Are Different from Anyone Else and So is Your Weight Loss Journey (2019) (Year: 2019).*

Flowers et al. "MicroRNAs associated with exercise and diet: a systematic review" Physiol Genomics, 2015, vol. 47, pp. 1-11.

Milagro et al. "High-Throughput Sequencing of microRNAs in Peripheral Blood Mononuclear Cells: Identification of Potential Weight Loss Biomarkers" PLOS ONE, Jan. 2013, vol. 8, issue 1, e54319, 10 pages.

Parr et al. "Circulating MicroRNA Responses between 'High' and 'Low' Responders to a 16-Wk Diet and Exercise Weight Loss Intervention" PLOS ONE, Apr. 21, 2016, vol. 11, No. 4, e152545, 14 pages.

Illumina "Infinium CoreExome-24 v1.1 BeadChip" Jan. 1, 2015, 2 pages, XP055299483.

Aoi et al., "Muscle-Enriched MicroRNA miR-486 Decreases in Circulation in Response to Exercise in Young Men", Frontiers in Physiology, vol. 4, Issue No. 80, Apr. 11, 2013, pp. 1-7.

Japan Patent Office Communication for Application No. P2018-559308, Dispatch No. 005079, dated Jan. 12, 2021, 14 pages.

* cited by examiner

SEQUENCE LISTING

```
<160> NUMBER OF SEQ ID NOS: 33

<210> SEQ ID NO 1
<211> LENGTH: 68
<212> TYPE: DNA
<213> ORGANISM: Homo sapiens
<220> FEATURE:
<221> NAME/KEY: source
<222> LOCATION: 1..68
<223> OTHER INFORMATION: /mol_type="unassigned DNA"
      /organism="Homo sapiens"

<400> SEQUENCE: 1
gcatcctgta ctgagctgcc ccgaggccct tcatgctgcc cagctcgggg cagctcagta    60
caggatac                                                            68

<210> SEQ ID NO 2
<211> LENGTH: 64
<212> TYPE: DNA
<213> ORGANISM: Homo sapiens
<220> FEATURE:
<221> NAME/KEY: source
<222> LOCATION: 1..64
<223> OTHER INFORMATION: /mol_type="unassigned DNA"
      /organism="Homo sapiens"

<400> SEQUENCE: 2
tcctgtactg agctgccccg agctgggcag catgaagggc ctcggggcag ctcagtacag    60
gatg                                                                64

<210> SEQ ID NO 3
<211> LENGTH: 51
<212> TYPE: DNA
<213> ORGANISM: Homo sapiens
<220> FEATURE:
```

<221> NAME/KEY: source
<222> LOCATION: 1..51
<223> OTHER INFORMATION: /mol_type="unassigned DNA"
      /organism="Homo sapiens"

<400> SEQUENCE: 3
tttggtagaa ttcaccagtg aagccgtctg ggcatggact tttctttgta g         51

<210> SEQ ID NO 4
<211> LENGTH: 51
<212> TYPE: DNA
<213> ORGANISM: Homo sapiens
<220> FEATURE:
<221> NAME/KEY: source
<222> LOCATION: 1..51
<223> OTHER INFORMATION: /mol_type="unassigned DNA"
      /organism="Homo sapiens"

<400> SEQUENCE: 4 gcacggggttg ggcgactcaa actttctgcc cttgtgtgtg tgtccatgaa t         51

<210> SEQ ID NO 5
<211> LENGTH: 51
<212> TYPE: DNA
<213> ORGANISM: Homo sapiens
<220> FEATURE:
<221> NAME/KEY: source
<222> LOCATION: 1..51
<223> OTHER INFORMATION: /mol_type="unassigned DNA"
      /organism="Homo sapiens"

<400> SEQUENCE: 5
tccgcccccc gcccccacca tttgcctcct cttccaccgc cgcctcctcc c         51

<210> SEQ ID NO 6
<211> LENGTH: 51
<212> TYPE: DNA
<213> ORGANISM: Homo sapiens
<220> FEATURE:
<221> NAME/KEY: source
<222> LOCATION: 1..51
<223> OTHER INFORMATION: /mol_type="unassigned DNA"
      /organism="Homo sapiens"

<400> SEQUENCE: 6
tgttggccag gctggtctcg aacttctgac ctcaagtgat ccgcccacct g         51

<210> SEQ ID NO 7
<211> LENGTH: 51
<212> TYPE: DNA
<213> ORGANISM: Homo sapiens
<220> FEATURE:
<221> NAME/KEY: source
<222> LOCATION: 1..51
<223> OTHER INFORMATION: /mol_type="unassigned DNA"
      /organism="Homo sapiens"

<400> SEQUENCE: 7
cttatagttt taatttgtat ttccctaatc actaatgatg ttgagcatat t         51

<210> SEQ ID NO 8
<211> LENGTH: 51
<212> TYPE: DNA
<213> ORGANISM: Homo sapiens
<220> FEATURE:
<221> NAME/KEY: source
<222> LOCATION: 1..51
<223> OTHER INFORMATION: /mol_type="unassigned DNA"
      /organism="Homo sapiens"

```
<400> SEQUENCE: 8
gacaaatgtc cttttcttc tttgaggtga tggcttcatg ggggtacaca t         51

<210> SEQ ID NO 9
<211> LENGTH: 51
<212> TYPE: DNA
<213> ORGANISM: Homo sapiens
<220> FEATURE:
<221> NAME/KEY: source
<222> LOCATION: 1..51
<223> OTHER INFORMATION: /mol_type="unassigned DNA"
      /organism="Homo sapiens"

<400> SEQUENCE: 9
tgcattactg cactccagcc tgggcgacag agcaagactc tgctttaaaa a         51

<210> SEQ ID NO 10
<211> LENGTH: 51
<212> TYPE: DNA
<213> ORGANISM: Homo sapiens
<220> FEATURE:
<221> NAME/KEY: source
<222> LOCATION: 1..51
<223> OTHER INFORMATION: /mol_type="unassigned DNA"
      /organism="Homo sapiens"

<400> SEQUENCE: 10
gattacaagc gtgaaccact gcacccggcc ttggcttgtg ttgtttctaa t         51

<210> SEQ ID NO 11
<211> LENGTH: 51
<212> TYPE: DNA
<213> ORGANISM: Homo sapiens
<220> FEATURE:
<221> NAME/KEY: source
<222> LOCATION: 1..51
<223> OTHER INFORMATION: /mol_type="unassigned DNA"
      /organism="Homo sapiens"

<400> SEQUENCE: 11
tgagtgaaag aagccaggct ttaaaaaaag agagagtgca tactgtatga a         51

<210> SEQ ID NO 12
<211> LENGTH: 51
<212> TYPE: DNA
<213> ORGANISM: Homo sapiens
<220> FEATURE:
<221> NAME/KEY: source
<222> LOCATION: 1..51
<223> OTHER INFORMATION: /mol_type="unassigned DNA"
      /organism="Homo sapiens"

<400> SEQUENCE: 12
catcctccac ccagccggag gggctgtcct tctcccttcc tgccttgttg g         51

<210> SEQ ID NO 13
<211> LENGTH: 51
<212> TYPE: DNA
<213> ORGANISM: Homo sapiens
<220> FEATURE:
<221> NAME/KEY: source
<222> LOCATION: 1..51
<223> OTHER INFORMATION: /mol_type="unassigned DNA"
      /organism="Homo sapiens"

<400> SEQUENCE: 13
ggctgctccc tgtctcaccc tatccgctcc cagccacccc agcatgatgt g         51
```

<210> SEQ ID NO 14
<211> LENGTH: 51
<212> TYPE: DNA
<213> ORGANISM: Homo sapiens
<220> FEATURE:
<221> NAME/KEY: source
<222> LOCATION: 1..51
<223> OTHER INFORMATION: /mol_type="unassigned DNA"
      /organism="Homo sapiens"

<400> SEQUENCE: 14
cattgcttaa tggaaaaccc tctgctagac agccctgaag gggccttggc a          51

<210> SEQ ID NO 15
<211> LENGTH: 51
<212> TYPE: DNA
<213> ORGANISM: Homo sapiens
<220> FEATURE:
<221> NAME/KEY: source
<222> LOCATION: 1..51
<223> OTHER INFORMATION: /mol_type="unassigned DNA"
      /organism="Homo sapiens"

<400> SEQUENCE: 15
tggggttgaa ccccagctct gccagatctc ccagctctcc cagccgggag a          51

<210> SEQ ID NO 16
<211> LENGTH: 51
<212> TYPE: DNA
<213> ORGANISM: Homo sapiens
<220> FEATURE:
<221> NAME/KEY: source
<222> LOCATION: 1..51
<223> OTHER INFORMATION: /mol_type="unassigned DNA"
      /organism="Homo sapiens"

<400> SEQUENCE: 16
tgcctccacc tctggtcggc cttccctgac ctccctatca gaatctcttc c          51

<210> SEQ ID NO 17
<211> LENGTH: 51
<212> TYPE: DNA
<213> ORGANISM: Homo sapiens
<220> FEATURE:
<221> NAME/KEY: source
<222> LOCATION: 1..51
<223> OTHER INFORMATION: /mol_type="unassigned DNA"
      /organism="Homo sapiens"

<400> SEQUENCE: 17
gtctctgtcc atctgtgctt tttgaggtct gcatatttcc ctgactagat t          51

<210> SEQ ID NO 18
<211> LENGTH: 51
<212> TYPE: DNA
<213> ORGANISM: Homo sapiens
<220> FEATURE:
<221> NAME/KEY: source
<222> LOCATION: 1..51
<223> OTHER INFORMATION: /mol_type="unassigned DNA"
      /organism="Homo sapiens"

<400> SEQUENCE: 18
aggggcaaca ggagttccct ctctgcccca gggatgtccc ttcaggtcac c          51

<210> SEQ ID NO 19
<211> LENGTH: 51

<212> TYPE: DNA
<213> ORGANISM: Homo sapiens
<220> FEATURE:
<221> NAME/KEY: source
<222> LOCATION: 1..51
<223> OTHER INFORMATION: /mol_type="unassigned DNA"
      /organism="Homo sapiens"

<400> SEQUENCE: 19
tgaattccct ccaccccgg cttccaccaa cttccttgct cttgagactc a         51

<210> SEQ ID NO 20
<211> LENGTH: 51
<212> TYPE: DNA
<213> ORGANISM: Homo sapiens
<220> FEATURE:
<221> NAME/KEY: source
<222> LOCATION: 1..51
<223> OTHER INFORMATION: /mol_type="unassigned DNA"
      /organism="Homo sapiens"

<400> SEQUENCE: 20
atggctgaga gggtggtgga gcccctgcc gggcactccg tcggtgctca g         51

<210> SEQ ID NO 21
<211> LENGTH: 51
<212> TYPE: DNA
<213> ORGANISM: Homo sapiens
<220> FEATURE:
<221> NAME/KEY: source
<222> LOCATION: 1..51
<223> OTHER INFORMATION: /mol_type="unassigned DNA"
      /organism="Homo sapiens"

<400> SEQUENCE: 21
cccctctaaa ggaagcaaaa gcagctccac ccccggccga caaggcgcct a         51

<210> SEQ ID NO 22
<211> LENGTH: 51
<212> TYPE: DNA
<213> ORGANISM: Homo sapiens
<220> FEATURE:
<221> NAME/KEY: source
<222> LOCATION: 1..51
<223> OTHER INFORMATION: /mol_type="unassigned DNA"
      /organism="Homo sapiens"

<400> SEQUENCE: 22
ttccgacaga tcagctgtca ttgcaggagg caggattgaa gcctggaggt c         51

<210> SEQ ID NO 23
<211> LENGTH: 51
<212> TYPE: DNA
<213> ORGANISM: Homo sapiens
<220> FEATURE:
<221> NAME/KEY: source
<222> LOCATION: 1..51
<223> OTHER INFORMATION: /mol_type="unassigned DNA"
      /organism="Homo sapiens"

<400> SEQUENCE: 23
tgaattcctt ctgagtgtgc aagtgctcca ggatgcctct ctgtatgggc c         51

<210> SEQ ID NO 24
<211> LENGTH: 51
<212> TYPE: DNA
<213> ORGANISM: Homo sapiens
<220> FEATURE:
<221> NAME/KEY: source
<222> LOCATION: 1..51
<223> OTHER INFORMATION: /mol_type="unassigned DNA"
      /organism="Homo sapiens"

<400> SEQUENCE: 24
gccatgcgcc agccttggga acccacggat ggagcggatg tgctccctgg c          51

<210> SEQ ID NO 25
<211> LENGTH: 51
<212> TYPE: DNA
<213> ORGANISM: Homo sapiens
<220> FEATURE:
<221> NAME/KEY: source
<222> LOCATION: 1..51
<223> OTHER INFORMATION: /mol_type="unassigned DNA"
      /organism="Homo sapiens"

<400> SEQUENCE: 25
tttctgttca ggagatggca gagtcaagtg ggtaagagca tgaactctgg a          51

<210> SEQ ID NO 26
<211> LENGTH: 51
<212> TYPE: DNA
<213> ORGANISM: Homo sapiens
<220> FEATURE:
<221> NAME/KEY: source
<222> LOCATION: 1..51
<223> OTHER INFORMATION: /mol_type="unassigned DNA"
      /organism="Homo sapiens"

<400> SEQUENCE: 26 attattttc ttattactct tgcgaacatt ttatattatt tacatcagtt a           51

<210> SEQ ID NO 27
<211> LENGTH: 51
<212> TYPE: DNA
<213> ORGANISM: Homo sapiens
<220> FEATURE:
<221> NAME/KEY: source
<222> LOCATION: 1..51
<223> OTHER INFORMATION: /mol_type="unassigned DNA"
      /organism="Homo sapiens"

<400> SEQUENCE: 27
ttcaccctgt tggccaggct ggtcttgaac tgctgacctc aagtgattcg c          51

<210> SEQ ID NO 28
<211> LENGTH: 51
<212> TYPE: DNA
<213> ORGANISM: Homo sapiens
<220> FEATURE:
<221> NAME/KEY: source
<222> LOCATION: 1..51
<223> OTHER INFORMATION: /mol_type="unassigned DNA"
      /organism="Homo sapiens"

<400> SEQUENCE: 28
tgctctgtct ggcgtggtgc ccgggtttga aatccctgat ggctgagagg g          51

<210> SEQ ID NO 29
<211> LENGTH: 51
<212> TYPE: DNA
<213> ORGANISM: Homo sapiens
<220> FEATURE:
<221> NAME/KEY: source
<222> LOCATION: 1..51
<223> OTHER INFORMATION: /mol_type="unassigned DNA"
      /organism="Homo sapiens"

```
<400> SEQUENCE: 29
cctgcacgca tgttcttgcc tccacttctg gtcggccttc cgtgacctcc c         51

<210> SEQ ID NO 30
<211> LENGTH: 51
<212> TYPE: DNA
<213> ORGANISM: Homo sapiens
<220> FEATURE:
<221> NAME/KEY: source
<222> LOCATION: 1..51
<223> OTHER INFORMATION: /mol_type="unassigned DNA"
      /organism="Homo sapiens"

<400> SEQUENCE: 30
ctacgtcttc gtctgagatg gctttaccac caggtcgcgt gccacagcca t         51

<210> SEQ ID NO 31
<211> LENGTH: 51
<212> TYPE: DNA
<213> ORGANISM: Homo sapiens
<220> FEATURE:
<221> NAME/KEY: source
<222> LOCATION: 1..51
<223> OTHER INFORMATION: /mol_type="unassigned DNA"
      /organism="Homo sapiens"

<400> SEQUENCE: 31
agtagcaaat gggggacag gtgtgttttt ggggttccct aggttggccc c          51

<210> SEQ ID NO 32
<211> LENGTH: 51
<212> TYPE: DNA
<213> ORGANISM: Homo sapiens
<220> FEATURE:
<221> NAME/KEY: source
<222> LOCATION: 1..51
<223> OTHER INFORMATION: /mol_type="unassigned DNA"
      /organism="Homo sapiens"

<400> SEQUENCE: 32
cccagggtca gggttggcat cgacatctct gtcctcactg ccaggcataa t         51

<210> SEQ ID NO 33
<211> LENGTH: 51
<212> TYPE: DNA
<213> ORGANISM: Homo sapiens
<220> FEATURE:
<221> NAME/KEY: source
<222> LOCATION: 1..51
<223> OTHER INFORMATION: /mol_type="unassigned DNA"
      /organism="Homo sapiens"

<400> SEQUENCE: 33
ggcaaccacc atgcctgccc ctctcactcc tgcagaggtt tccaggacac c         51
```

BIOMARKERS FOR PREDICTING DEGREE OF WEIGHT LOSS

CROSS REFERENCE TO RELATED APPLICATIONS

The present application is a National Stage of International Application No. PCT/EP2017/062942, filed on May 30, 2017, which claims priority to European Patent Application No. 16172242.6, filed on May 31, 2016, the entire contents of which are being incorporated herein by reference.

FIELD OF INVENTION

The present invention provides a number of biomarkers and biomarker combinations that can be used to predict the degree of weight loss attainable by applying one or more dietary interventions to a subject and/or the degree of maintenance of weight loss following one or more dietary interventions. The present invention also provides a number of biomarkers and biomarker combinations that can be used to predict the degree of improvement in glycemic control attainable by applying one or more dietary interventions to a subject.

BACKGROUND

Obesity is a chronic metabolic disorder that has reached epidemic proportions in many areas of the world. Obesity is the major risk factor for serious co-morbidities such as type 2 diabetes mellitus, cardiovascular disease, dyslipidaemia and certain types of cancer (World Health Organ Tech Rep Ser. 2000; 894:i-xii, 1-253).

It has long been recognized that low calorie dietary interventions can be very efficient in reducing weight and that this weight loss is generally accompanied by an improvement for the risk of obesity related co-morbidities, in particular type 2 diabetes mellitus (World Health Organ Tech Rep Ser. 2000; 894:i-xii, 1-253). Empirical data suggests that a weight loss of at least 10% of the initial weight results in a considerable decrease in risk for obesity related co-morbidities (World Health Organ Tech Rep Ser. 2000; 894:i-xii, 1-253). However, the capacity to lose weight shows large inter-subject variability.

Some studies (e.g. Ghosh, S. et al., Obesity (Silver Spring), (2011) 19(2):457-463) illustrate that a percentage of the population do not successfully lose weight on a low calorie diet. This leads to an unrealistic expectation of weight loss, which in turn causes non-compliance, drop-outs and generally unsuccessful dietary intervention.

Some studies also demonstrate that there are methods in the art for monitoring weight loss which include monitoring levels of particular biomarkers in plasma (e.g. Lijnen et al., Thromb Res. 2012 January, 129(1): 74-9; Cugno et al., Intern Emerg Med. 2012 June, 7(3): 237-42; and Bladbjerg et al., Br J Nutr. 2010 December, 104(12): 1824-30). However, these methods do not provide a prediction or indication of the degree of weight loss attainable by a particular subject. There is no predictive value in looking at the correlation of biomarker levels with weight loss.

Keeping weight lost stable also presents a major challenge to the patient. It is known that only one year after a weight loss intervention, about one-third of the lost weight is regained (Hensrud, Obes. Res. 9 Suppl 4, 348S-353S, 2001). Moreover, diet-induced weight loss induces several physiological changes that facilitate weight regain (Sumithran and Proietto., Clin. Sci. Lond. Engl. 1979 124, 231-241 (2013)). These changes include alterations in energy expenditure, substrate metabolism and hormone pathways involved in appetite regulation. Our understanding of these physiological and molecular changes remains so far limited.

The solution for successful planning and design of dietary interventions, for example low calorie diets, lies in the availability of a method which predicts a weight loss trajectory. Such a method would be useful to assist in modifying a subject's lifestyle, e.g. by a change in diet, and also to stratify subjects into adapted treatment groups according to their biological weight loss capacity.

United States Patent Application US 2011/0124121 discloses a method for predicting weight loss success. The methods disclosed comprises selecting a patient who is undergoing or considering undergoing a weight loss therapy such as gastric banding, measuring one or more hormone responses of the patient to caloric intake and predicting success of a weight loss therapy based on the hormone response. The hormones measured are gastrointestinal hormones such as a pancreatic hormone.

European Patent Application EP 2 420 843 discloses a method for determining the probability that a person will maintain weight loss after an intentional weight loss by determining the level of angiotensin I converting enzyme (ACE) before and after the dietary period.

There is, however, still a need for a method of accurately predicting the degree of weight loss in a subject. Consequently, it was the objective of the present invention to provide biomarkers that can be detected easily and that can facilitate the prediction of weight loss in a subject. Such biomarkers can be used to predict weight trajectory of a subject prior to a dietary intervention.

These biomarkers can be used to optimise dietary intervention and assist in lifestyle modifications.

SUMMARY OF THE INVENTION

The present invention identifies biomarkers useful in predicting the predisposition of a subject to change in weight-related phenotypes by applying one or more dietary interventions to a subject. The present invention also identifies biomarkers useful in predicting the predisposition of a subject to maintenance of weight-related phenotypes following one or more dietary interventions. Further, the present invention also identifies biomarkers useful in predicting the predisposition of a subject to improve glycemic control following one or more dietary interventions.

Accordingly the present invention provides in one aspect a method for predicting the degree of weight loss attainable by applying one or more dietary interventions to a subject and/or the degree of maintenance of weight loss following one or more dietary interventions; which method comprises determining the level of microRNA-486 (miR-486) in one or more samples obtained from the subject; and/or determining the nucleotide of the subject at one or more polymorphic positions genetically linked to miR-486.

In another aspect the present invention provides a method for predicting the degree of improvement in glycemic control attainable by applying one or more dietary interventions to a subject; which method comprises determining the level of miR-486 in one or more samples obtained from the subject and/or determining the nucleotide of the subject at one or more polymorphic positions genetically linked to miR-486.

In one embodiment, the polymorphic position(s) which is genetically linked to miR-486 (e.g. SNP) is physically located less than 200, 150, 100, 75, 50, 25, 20, 15, 10, 5, 4, 3, 2, 1 kilobases (kb) from the miR-486 locus. Any SNP with LD r-square greater than 40% can also be considered as genetically linked.

In one embodiment the one or more polymorphic positions genetically linked to miR-486 is a polymorphic position shown in Table 1 or Table 2.

In one embodiment the one or more polymorphic positions are selected from:
(i) position 26 of SEQ ID NO: 3 (rs545936)
(ii) position 26 of SEQ ID NO: 4 (rs6981587); and
(iii) position 26 of SEQ ID NO: 5 (rs190249167).

The method may comprise determining the presence of G at position 26 of SEQ ID NO: 3; and/or C at position 26 of SEQ ID NO: 4; and/or C at position 26 of SEQ ID NO: 5. In one embodiment, determining the presence of G at position 26 of SEQ ID NO: 3; and/or C at position 26 of SEQ ID NO: 4; and/or C at position 26 of SEQ ID NO: 5 is indicative that the subject is predicted to lose more weight following the application of one or more dietary interventions and/or a that the subject is predicted to better maintain weight loss and/or that the subject is predicted to better improve glycemic control following the application of one or more dietary interventions to the subject.

In one embodiment the method comprises determining the presence of a genotype selected from:
(i) G/G (homozygous) at position 26 of SEQ ID NO: 3; or
(ii) A/G (heterozygous) at position 26 of SEQ ID NO: 3;
and wherein the presence of said genotype indicates that, relative to subjects with G/G genotype, a subject is predicted to lose more weight following the application of one or more dietary interventions to the subject and/or that a subject is predicted to better maintain weight loss and/or that a subject is predicted to better improve glycemic control following the application of one or more dietary interventions to the subject.

In one embodiment the method comprises determining the presence of a genotype selected from:
(i) C/C (homozygous) at position 26 of SEQ ID NO: 4; or
(ii) C/T (heterozygous) at position 26 of SEQ ID NO: 4;
and wherein the presence of said genotype indicates that, relative to subjects with T/T genotype, a subject is predicted to lose more weight following the application of one or more dietary interventions to the subject and/or that a subject is predicted to better maintain weight loss and/or that a subject is predicted to better improve glycemic control following the application of one or more dietary interventions to the subject.

In one embodiment the method comprises determining the presence of a genotype selected from:
(i) C/C (homozygous) at position 26 of SEQ ID NO: 5; or
(ii) C/T (heterozygous) at position 26 of SEQ ID NO: 5;
and wherein the presence of said genotype indicates that, relative to subjects with T/T genotype, a subject is predicted to lose more weight following the application of one or more dietary interventions to the subject and/or that a subject is predicted to better maintain weight loss and/or that a subject is predicted to better improve glycemic control following the application of one or more dietary interventions to the subject.

The one or more samples may be derived from blood, saliva, urine, muscle or adipose tissue.

The dietary intervention may be a low calorie diet.

The dietary intervention may comprise administering at least one diet product to the subject.

A low calorie diet may comprise a decreased consumption of fat and/or an increase in consumption of low fat foods. By way of example only, low fat foods may include wholemeal flour and bread, porridge oats, high-fibre breakfast cereals, wholegrain rice and pasta, vegetables and fruit, dried beans and lentils, baked potatoes, dried fruit, walnuts, white fish, herring, mackerel, sardines, kippers, pilchards, salmon and lean white meat.

In one embodiment the low calorie diet may comprises a calorie intake of about 600 to about 1200 kcal/day and/or may comprise administration of at least one diet product.

The low calorie diet may also comprise administration of up to, for example, about 400 g vegetables/day.

Preferably the diet product is Optifast® or Modifast®.

Thus, the diet may comprise a product such as Optifast® or Modifast®. This may be supplemented with three portions of non-starchy vegetables such that the total energy intake is about 2.5 MJ (600 kcal/day). This may be further supplemented with at least 2 L of water or other energy free beverages per day.

In another embodiment, the diet may comprise, for example, a composition which is 46.4% carbohydrate, 32.5% protein and 20.1% with fat, vitamins, minerals and trace elements; 2.1 MJ per day (510 kcal/day); This may be supplemented with three portions of non-starchy vegetables such that the total energy intake is about 2.5 MJ (600 kcal/day). This may be further supplemented with at least 2 L of water or other energy free beverages per day.

In one embodiment, the low calorie diet has a duration of up to 16 weeks, e.g. 4 to 16 weeks.

The methods referred to herein may further comprise determining one or more anthropometric measures and/or lifestyle characteristics of the subject.

The anthropometric measure may be selected from, for example, the group consisting of gender, weight, height, age and body mass index, and the lifestyle characteristic may be, for example, whether the subject is a smoker or a non-smoker.

According to another aspect of the present invention there is provided a method for optimizing one or more dietary interventions for a subject comprising:
assessing the predisposition of a subject to weight loss attainable by one or more dietary interventions and/or the predisposition of a subject to maintenance of weight loss and/or the improvement of glycemic control attainable following one or more dietary interventions according to the method defined herein; and
applying one or more dietary interventions to the subject.

According to another aspect of the present invention there is provided a method for selecting a modification of lifestyle of a subject, the method comprising:
a. performing a method of assessing the predisposition of a subject to weight loss attainable by one or more dietary interventions and/or the predisposition of a subject to maintenance of weight loss and/or the improvement of glycemic control attainable following one or more dietary interventions according to the method defined herein; and
b. selecting a suitable modification in lifestyle based upon the predicted weight loss attainable and/or predicted maintenance of weight loss and/or the improvement of glycemic control attainable from (a).

In one embodiment, the modification of lifestyle comprises a dietary intervention, preferably a dietary intervention defined herein.

According to another aspect of the present invention there is provided a low calorie diet for weight loss, wherein the diet product is administered to a subject that is predicted to attain weight loss by the method defined herein.

According to another aspect of the present invention there is provided a diet product for use as part of a low calorie diet for weight loss, wherein the diet product is administered to a subject that is predicted to attain weight loss or maintenance by the method defend herein.

According to another aspect of the present invention there is provided a diet product for use as part of a low calorie diet for weight loss, wherein the diet product is administered to a subject that is predicted to attain both weight maintenance and weight loss by the method defined herein.

According to another aspect of the present invention there is provided a diet product for use in treating obesity or an obesity-related disorder, wherein the diet product is administered to a subject that is predicted to attain weight maintenance and/or weight loss by the method defined herein.

In one embodiment, the diet product may comprise a product such as Optifast® or Modifast®.

In another embodiment, the diet product may comprise, for example, a composition which is 46.4% carbohydrate, 32.5% protein and 20.1% with fat, vitamins, minerals and trace elements; 2.1 MJ per day (510 kcal/day); This may be supplemented with three portions of non-starchy vegetables such that the total energy intake is about 2.5 MJ (600 kcal/day). This may be further supplemented with at least 2 L of water or other energy free beverages per day.

In another aspect the present invention provides an allele-specific oligonucleotide probe capable of detecting a polymorphic position shown in Table 1 or Table 2.

In a further aspect the present invention provides an allele-specific primer capable of detecting a polymorphic position shown in Table 1 or Table 2.

The allele-specific oligonucleotide probe or an allele-specific primer may be capable of detecting a polymorphic position selected from:
(i) position 26 of SEQ ID NO: 3 (rs545936)
(ii) position 26 of SEQ ID NO: 4 (rs6981587)
(iii) position 26 of SEQ ID NO: 5 (rs190249167).

In another aspect the present invention provides a diagnostic kit comprising two or more allele-specific oligonucleotide primers and/or an allele-specific oligonucleotide probes provided by the present invention.

The diagnostic kit may comprise two or more allele-specific oligonucleotide primers and/or allele-specific oligonucleotide probes capable of determining the presence of G at position 26 of SEQ ID NO: 3; and/or C at position 26 of SEQ ID NO: 4; and/or C at position 26 of SEQ ID NO: 5.

DETAILED DESCRIPTION OF THE INVENTION

Predicting the Degree of Weight Loss

Figure 1:
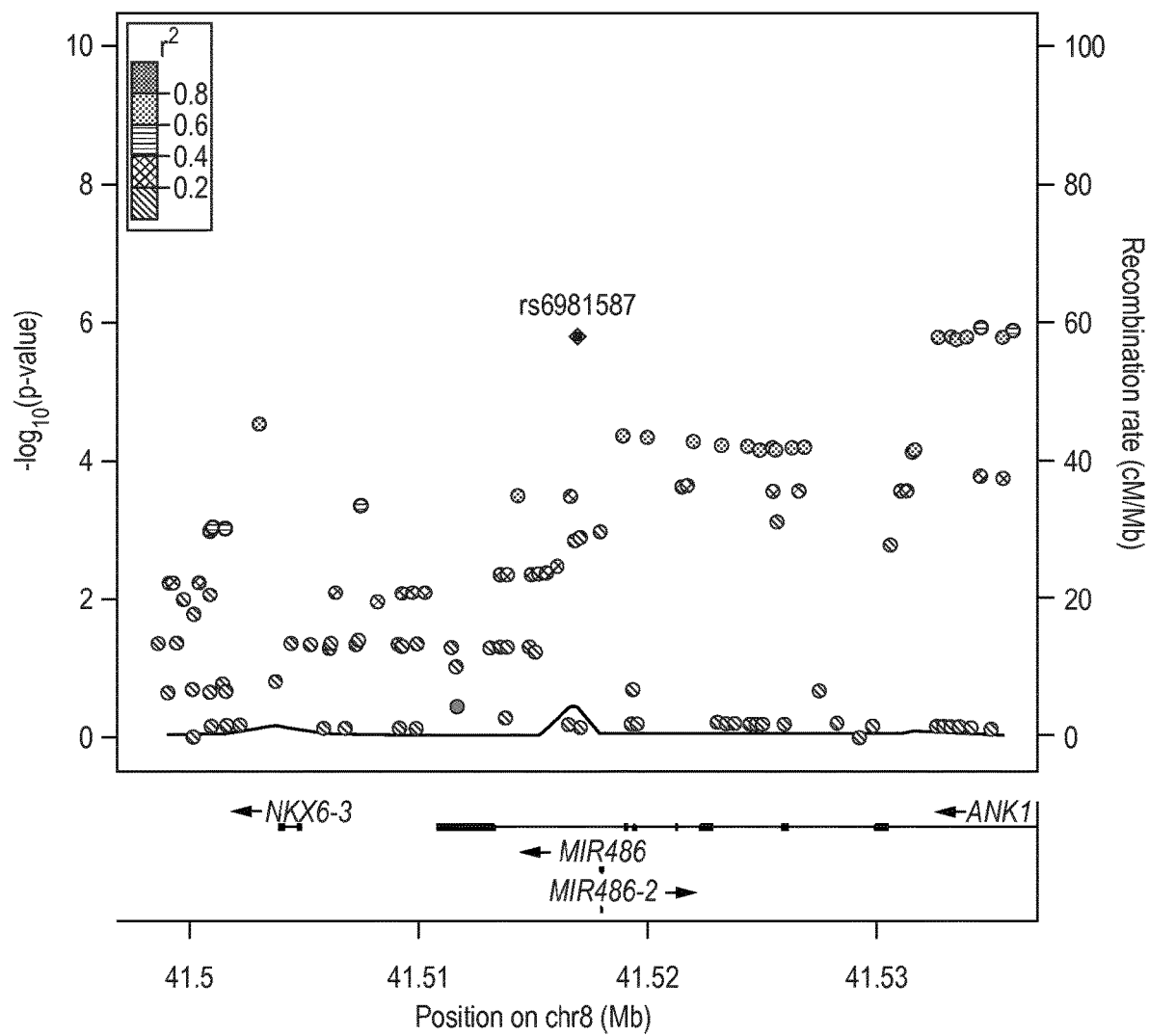
FIG. 1—SNPs near miR-486 predict weight loss after low-caloric diet

The present invention relates in one aspect to a method for predicting the degree of weight loss attainable by applying one or more dietary interventions to a subject and/or the degree of maintenance of weight loss following one or more dietary interventions. The invention allows accurate prediction of weight trajectory of a patient, prior to a weight loss intervention and/or prior to a weight maintenance intervention.

The method may be used to make an informed prediction of the subject's capacity to lose weight and/or maintain weight loss, and select or adjust one or more dietary intervention accordingly.

For example, the present invention can be used for predicting the outcome of a weight management program, for adapting the weight management program and for stratifying patients following such a program into groups of successful or less successful profiles. For example, the method can be used to identify subjects with either a "high" or "low" likelihood of achieving weight loss by applying a dietary intervention. Similarly, the method can be used to identify subjects with either a "high" or "low" likelihood of maintaining weight loss following a dietary intervention.

In particular embodiments, the method may be used to make an informed prediction of the subject's capacity to lose weight, and select or adjust one or more dietary intervention accordingly. For example, where the dietary intervention is a low calorie diet, the method could be used to select the appropriate diet for the subject or to adjust the daily calorie intake or duration of a particular diet to affect the degree of weight loss, or to increase compliance to the low calorie diet by setting realistic expectations for the subject. The method may also be used to assist in modifying the lifestyle of a subject.

The method provides a skilled person with a useful tool for assessing which subjects will most likely benefit from a particular dietary intervention, e.g. a low calorie diet. The present method therefore enables dietary interventions such as a low calorie diet and modifications in lifestyle to be optimised.

Weight loss as defined herein may refer to a reduction in parameters such as weight (e.g. in kilograms), body mass index ($kgm^{-2}$), or waist circumference (e.g. in centimetres), or waist-hip ratio (e.g. in centimetres). Weight loss may be calculated by subtracting the value of one or more of the aforementioned parameters at the end of the dietary intervention from the value of said parameter at the onset of the dietary intervention. Preferably, the degree of weight loss is represented by the body mass index that a subject is predicted to attain by applying the dietary intervention.

The degree of weight loss may be expressed as a percentage of a subject's body weight (e.g. in kilograms) or body mass index ($kgm^{-2}$). For example, a subject may be predicted to lose at least 10% of their initial body weight, at least 8% of their initial body weight, or at least 5% of their initial body weight. By way of example only, a subject may be predicted to lose between 5 and 10% of their initial body weight.

In one embodiment, a degree of weight loss of at least 10% of initial body weight results in a considerable decrease in risk for obesity related co-morbidities.

Weight maintenance as defined herein may refer to the maintenance in parameters such as weight (e.g. in kilograms), body mass index ($kgm^{-2}$), waist-hip ratio (e.g. in centimetres) fat mass (e.g. in kilograms), hip circumference (e.g. in centimetres) or waist circumference (e.g. in centimetres) following a dietary intervention The degree of weight maintenance may be calculated by determining the change in one or more of the aforementioned parameters during a period of time following the end of the dietary intervention. The period of time may be for example at least 4, 8, 12, 16, 20, 24, 28, 32, 36, 40, 44, 48 or 52 weeks following the end of the dietary intervention.

The degree of weight maintenance may be expressed as the percentage of weight change during a period following the end of the dietary intervention. For example, a subject predisposed to weight maintenance may be likely to regain less than 50, 40, 30, 20, 10, 5% or 1% of the weight lost during the dietary intervention.

Predicting the Degree of Glycemic Control Improvement

The present invention relates in one aspect to a method for predicting the degree of glycemic control improvement attainable by applying one or more dietary interventions to a subject. The invention allows accurate prediction of glycemic control trajectory of a patient, prior to a weight loss intervention and/or prior to a weight maintenance intervention.

The method may be used to make an informed prediction of the subject's capacity to improve glycemic control, and select or adjust one or more dietary intervention accordingly.

In particular embodiments, the method may be used to make an informed prediction of the subject's capacity to improve glycemic control, and select or adjust one or more dietary intervention accordingly. For example, where the dietary intervention is a low calorie diet, the method could be used to select the appropriate diet for the subject or to adjust the daily calorie intake or duration of a particular diet to affect the degree of glycemic control improvement, or to increase compliance to the low calorie diet by setting realistic expectations for the subject. The method may also be used to assist in modifying the lifestyle of a subject.

The method provides a skilled person with a useful tool for assessing which subjects will most likely benefit from a particular dietary intervention, e.g. a low calorie diet. The present method therefore enables dietary interventions such as a low calorie diet and modifications in lifestyle to be optimised.

Glycemic control as defined herein may refer to the control of levels of blood glucose in a subject.

Glucose is the primary source of energy for the body and the body naturally regulates blood glucose levels tightly as a part of metabolic homeostasis. Exogenous glucose is absorbed from the intestines and together with endogenous glucose it circulates into the bloodstream where cells have access to the glucose. Cells in skeletal muscle as well as liver and adipose tissue use glucose depending on the action of insulin, produced by β cells in the pancreas.

If blood sugar levels are too high the body suppresses appetite over the short term. However, long-term high blood sugar levels (hyperglycemia) causes many health problems including heart disease, eye, kidney, and nerve damage.

Blood glucose levels within a given range are typically associated with good health. Hyperglycemia may be associated with conditions such as insulin resistance, prediabetes, type 2 diabetes, metabolic syndrome or cardiovascular disease. In contrast, very low blood sugar levels may lead to potentially fatal hypoglycemia. Hypoglycemia may be associated with symptoms such as lethargy, impaired mental functioning; irritability; shaking, twitching, weakness in arm and leg muscles; pale complexion; sweating; paranoid or aggressive mentality and loss of consciousness.

Glucose levels and glycemic control may be determined, for example, measuring the fasting plasma glucose (FPG) concentration as well as glycated hemoglobin (HbA1c), oral glucose tolerance test (OGTT), Homeostasis model assessment of insulin-resistance (HOMA-IR) or the Matsuda Index.

Glucose levels, as determined using an FPG or OGTT test for example, are typically determined using blood serum or plasma. Techniques for collecting blood samples and separating blood fractions are well known in the art. For instance, vena blood samples can be collected from patients using a needle and deposited into plastic tubes. The collection tubes may, for example, contain spray-coated silica and a polymer gel for serum separation. Serum can be separated by centrifugation at 1300 RCF for 10 min at room temperature and stored in small plastic tubes at −80° C.

Improvement in glycemic control may be referred to herein by a reduction in parameters such as FPG levels, OGTT glucose levels, HbA1c percentages, HOMA-IR or Matsuda Index scores.

The FPG test comprises determining the fasting blood glucose level of a subject about 8 to 14 hours, for example 8, 12, or 14 hours, after eating. The World Health Organisations defines the following fasting glucose test results:

Normal: Below 6.1 mmol/l (110 mg/dl)

Impaired fasting glucose: Between 6.1 and 6.9 mmol/l (between 111 mg/dl and 125 mg/dl)

Diabetic: 7.0 mmol/l and above (126 mg/dl and above)

In one embodiment, the degree of improvement in glycemic control may be expressed as a percentage of the subject's FPG level. For example, the FPG of a subject may be predicted to be reduced by at least 0.5%, at least 1%, at least 2%, at least 3%, at least 5%, at least 7%, or at least 10% compared to the FPG levels prior to the dietary intervention.

The HbA1c test comprises determining the percentage of glycated hemoglobin of a subject at any time of a day. The World Health Organisation has a HbA1c of 6.5% as the recommended cutoff point for diagnosing diabetes and a value of less than 6.5% does not exclude diabetes which may still be diagnosed using glucose tests.

In one embodiment, the degree of improvement in glycemic control may be expressed as a percentage of the subject's HbA1c percentage. For example, the HbA1c percentage of a subject may be predicted to be reduced by at least 0.5%, at least 1%, at least 2%, at least 3%, at least 5%, at least 7%, or at least 10% compared to the HbA1c levels prior to the dietary intervention.

The HOMA-IR score is derived from fasting glucose and insulin levels (Matthews et al.; 1985; Diabetologia.; 28(7): 412-419). Higher HOMA-IR scores indicate lower insulin-sensitivity.

Cut-points for defining insulin-resistance can be population, age and sex dependent (Gayoso-Diz et al. BMC Endocrine Disorder4s 2013, 13:47). For e.g. in a large study of 17 European populations (Stern et al.; 2005; Diabetes; 54:333-339), diagnose of insulin resistance was defined as:

BMI>28.9 kg/m2 and HOMA-IR>4.65

BMI>27.5 kg/m2 and HOMA-IR>3.60

In clinical practices, HOMA-IR>3 (or sometimes >2) defines insulin-resistance; with HOMA-IR>5 defining severe insulin-resistance.

In one embodiment, the degree of improvement in glycemic control may be expressed as a percentage of the subject's HOMA-IR. For example, the HOMA-IR percentage of a subject may be predicted to be reduced by at least 0.5%, at least 1%, at least 2%, at least 3%, at least 5%, at least 7%, or at least 10% compared to the HOMA-IR levels prior to the dietary intervention.

The OGTT involves administering oral glucose to a subject and determining how quickly it is cleared from the blood. Typically, a zero time (baseline) blood sample is drawn to enable a baseline glucose and/or insulin level to be determined, the subject is then administered an oral glucose dose within five minutes of the zero time, and subsequent blood glucose levels are determined at intervals following glucose administration. The glucose dose is typically 75 g and results are usually determined based on the glucose level 1 or 2 hours post glucose consumption.

A 1 hour glucose level below 10 mmol/L (180 mg/dL) is typically considered normal. A 2 hour glucose level below 7.8 mmol/L (140 mg/dL) is normal, whereas higher glucose levels indicate hyperglycemia. Blood plasma glucose between 7.8 mmol/L (140 mg/dL) and 11.1 mmol/L (200 mg/dL) indicate "impaired glucose tolerance", and levels above 11.1 mmol/L (200 mg/dL) at 2 hours confirm a diagnosis of diabetes.

In one embodiment, the degree of improvement in glycemic control may be expressed as a percentage of the subject's OGTT glucose level. For example, the OGTT glucose level of a subject may be predicted to be reduced by at least 0.5%, at least 1%, at least 2%, at least 3%, at least 5%, at least 7%, or at least 10% compared to the OGTT glucose levels prior to the dietary intervention.

The Matsuda Index is a composite index, which evaluates whole body physiological insulin sensitivity from the data obtained by oral glucose tolerance test as described herein (Matsuda et al.; 1999; Diabetes Care; 22:1462-1740).

Accordingly, the Matsuda Index provides a composite of the OGTT and insulin sensitivity levels. Calculations for the Matsuda Index are based on insulin values given in microunits per milliliter (µU/mL) and those of glucose, in milligrams per deciliter (mg/L) obtained from the OGTT and the corresponding fasting values. The index of whole-body insulin sensitivity combines both hepatic and peripheral tissue insulin sensitivity. This index is calculated from plasma glucose (mg/dl) and insulin (mIU/1) concentrations in the fasting state and during OGTT.

$$ISI_{(MATSUDA)} = 1000/\sqrt{G_0 I_0 G_{MEAN} I_{MEAN}}$$

$I_0$—Fasting plasma insulin concentration (mIU/1),
$G_0$—Fasting plasma glucose concentration (mg/dl),
$G_{mean}$—Mean plasma glucose concentration during OGTT (mg/dl),
$I_{mean}$—Mean plasma insulin concentration during OGTT (mU/l),
10,000—Simplifying constant to get numbers from 0 to 12.
$\sqrt{}$—Correction of the nonlinear values distribution.

In one embodiment, the degree of improvement in glycemic control may be expressed as a percentage of the subject's Matsuda Index Score. For example, the Matsuda Index Score of a subject may be predicted to be increased by at least 0.5%, at least 1%, at least 2%, at least 3%, at least 5%, at least 7%, or at least 10% compared to the Matsuda Index Score prior to the dietary intervention.

The degree of improvement in glycemic control may be calculated by determining the change in one or more of the aforementioned parameters during a period of time following the end of the dietary intervention. The period of time may be for example at least 4, 8, 12, 16, 20, 24, 28, 32, 36, 40, 44, 48 or 52 weeks following the end of the dietary intervention.

Subject

Preferably the subject is a mammal, preferably a human. The subject may alternatively be a non-human mammal, including for example, a horse, cow, sheep or pig. In one embodiment, the subject is a companion animal such as a dog or a cat.

Sample

The present invention comprises a step of determining the level of one or more biomarkers in one or more samples obtained from a subject.

Preferably the sample is derived from blood, saliva or urine. More preferably the sample is derived from blood. The sample may contain a blood fraction or may be wholly blood. The sample preferably comprises blood plasma or serum, most preferably blood plasma. Techniques for collecting samples from a subject are well known in the art.

The sample may be an adipose tissue sample or skeletal muscle sample.

The invention includes the detection of the biomarkers as defined herein from a sample (which may be as defined above) that has already been removed from the individual.

Dietary Intervention

By the term "dietary intervention" is meant an external factor applied to a subject which causes a change in the subject's diet. In one embodiment, the dietary intervention is a low calorie diet.

Preferably the low calorie diet comprises a calorie intake of about 600 to about 1500 kcal/day, more preferably about 600 to about 1200 kcal/day, most preferably about 800 kcal/day. In one embodiment, the low calorie diet may comprise a predetermined amount (in grams) of vegetables per day, preferably up to about 400 g vegetables/day, e.g. about 200 g vegetables/day.

The low calorie diet may comprise administration of at least one diet product. The diet product may be a meal replacement product or a supplement product which may e.g. suppress the subject's appetite. The diet product can include food products, drinks, pet food products, food supplements, nutraceuticals, food additives or nutritional formulas.

In one embodiment, the diet may comprise a product such as Optifast® or Modifast®. This may be supplemented with three portions of non-starchy vegetables such that the total energy intake is about 2.5 MJ (600 kcal/day). This may be further supplemented with at least 2 L of water or other energy free beverages per day.

In another embodiment, the diet may comprise, for example, a composition which is 46.4% carbohydrate, 32.5% protein and 20.1% with fat, vitamins, minerals and trace elements; 2.1 MJ per day (510 kcal/day); This may be supplemented with three portions of non-starchy vegetables such that the total energy intake is about 2.5 MJ (600 kcal/day). This may be further supplemented with at least 2 L of water or other energy free beverages per day.

In one embodiment, the low calorie diet has a duration of up to 12 weeks. Preferably the low calorie diet has a duration of between 6 and 12 weeks, preferably between 8 and 10 weeks, e.g. 8 weeks.

Biomarkers miR-486 microRNAs (miRNAs) are short (e.g. 20-24 nt) non-coding RNAs that are involved in post-transcriptional regulation of gene expression in multicellular organisms by affecting both the stability and translation of mRNAs.

There are two miR-486 isoforms in humans; hsa-miR-486-1 (miR-486-1) and hsa-miR-486-2 (miR-486-2).

An illustrative miR-486-1 sequence is identified by Accession Number NR_030161.1 and shown herein as SEQ ID NO: 1.

SEQ ID NO: 1
GCATCCTGTACTGAGCTGCCCCGAGGCCCTTCATGCTGCCCAGCTCGGGG
CAGCTCAGTACAGGATAC

An illustrative miR-486-2 sequence is identified by Accession Number NR_106984.1 and shown herein as SEQ ID NO: 2.

SEQ ID NO: 2
TCCTGTACTGAGCTGCCCCGAGCTGGGCAGCATGAAGGGCCTCGGGGCAG
CTCAGTACAGGATG

As used herein, the term miR-486 may refer to miR-486-1 or miR-486-2.

It will be apparent to the person skilled in the art that there are a large number of methods which may be used to determine the level of a miRNA, for example, miR-486 in a sample.

By way of example, methods for isolating RNA from a sample are known in the art and include, for example, commercial RNA isolation kits such as the mirVana PARIS kit (Ambion) and Trizol LS (Invitrogen). The isolation of RNA (including miRNAs) may be performed in the presence of a strong denaturant such as guanidine thiocyanate, LiCl, sodium dodecyl sulfate and/or phenol in order to activate RNase, if present. It is also possible to process a sample for detection of miRNA sequences without prior isolation of the RNA, for example by isolating vesicles such as microvesicles from a sample.

Methods for detection of a miRNA in a sample are known in the art and include, but are not limited to, northern blotting (Virallyay et al; 2008; Nature Protocols; 3; 190-196), microarrays (Barad et al; 2004; Genome Res; 14(12): 2486-94), in situ hybridization (Song et al; 2010; Methods Mol Biol; 629: 287-294), single molecule detection in liquid phase (Arata et al; 2012; PLoS ONE; 7(11): e48329), massively parallel sequencing (Eminaga et al; 2013; Curr Protoc Mol Biol; 103:4.17-4.17.14) and quantitative polymerase chain reaction (qPCR) (Varkonyi-Gasic et al.; 2005;

The RNA in a sample may be amplified prior to the detection of miRNA sequences. Methods for amplification of RNA in a sample are known in the art and include reverse-transcription PCR (RT-PCR), Nucleic Acid Sequence Based Amplification (NASBA).

Primers for RT-PCR mediated cDNA synthesis may be provided by the provision of a shared sequence to all miRNA sequences such as, for example, a poly(A)-tail by ligation or through action of a Terminal Transferase, followed by annealing of an adaptor-oligod(T) primer.

Further methods comprise the use of a stem-loop primer and/or the use of a miRNA-specific primer.

Polymorphic Positions

The term "polymorphism" refers to two or more alternate forms (alleles) in a population of a genetic locus that differ in nucleotide sequence or have variable numbers of repeated nucleotide units. Polymorphisms occur in coding regions (exons), non-coding regions of genes or outside of genes (intergenic regions).

An "allele" is a particular form of a gene, genetic marker or other genetic locus, that is distinguishable from other forms of the gene, genetic marker or other genetic locus. The term allele includes, for example and without limitation, one form of a single nucleotide polymorphism (SNP). An individual can be homozygous for a certain allele in diploid cells; i.e. the allele on both paired chromosomes is identical; or heterozygous for said allele; i.e. the alleles on both paired chromosomes are not identical.

The term "gene" refers to a unit of DNA which performs one function. Usually, this is equated with the production of one RNA or one protein. A gene may contain coding regions, introns, untranslated regions and control regions.

As used herein, the phrase "genetic marker" refers to a feature of an individual's genome (e.g., a nucleotide or a polynucleotide sequence that is present in an individual's genome) that is associated with one or more loci of interest. Typically, a genetic marker is polymorphic and the variant forms of genetic markers include, for example, single nucleotide polymorphisms (SNPs), indels (i.e., insertions/deletions), simple sequence repeats (SSRs), restriction fragment length polymorphisms (RFLPs), random amplified polymorphic DNAs (RAPDs), cleaved amplified polymorphic sequence (CAPS) markers, Diversity Arrays Technology (DArT) markers, and amplified fragment length polymorphisms (AFLPs), Microsatellites or Simple sequence repeat (SSRs) among many other examples.

A "single nucleotide polymorphism (SNP)" is a DNA sequence variation occurring when a single nucleotide—A (for Adenine), T (for Thymine), C (for Cytosine), or G (for Guanine)—in the genome (or other sequence shared between individuals of a species) differs between individuals of a species (or between paired chromosomes in an individual).

A "genotype" as used herein refers to the combination of both alleles of a genetic marker, e.g. without limitation of a SNP, on a single genetic locus on paired (homologous) chromosomes in an individual.

The term "haplotype" refers to variants or alleles from distinct markers (e.g. SNPs) that are co-located on the same chromosome.

"Linkage disequilibrium" (also called "allelic association") refers to a phenomenon wherein particular alleles at two or more loci tend to remain together in linkage groups when segregating from parents to offspring with a greater frequency than expected from their individual frequencies in a given population.

In one aspect the present invention provides a method for predicting the degree of weight loss attainable by applying one or more dietary interventions to a subject and/or the degree of maintenance of weight loss following one or more dietary interventions; which method comprises determining the level of microRNA-486 (miR-486) in one or more samples obtained from the subject; and/or determining the nucleotide of the subject at one or more polymorphic positions genetically linked to miR-486.

In another aspect the present invention provides a method for predicting the degree of improvement in glycemic control attainable by applying one or more dietary interventions to a subject; which method comprises determining the level of microRNA-486 (miR-486) in one or more samples obtained from the subject; and/or determining the nucleotide of the subject at one or more polymorphic positions genetically linked to miR-486.

The polymorphic site may be one which has an association with weight loss attainable by applying one or more dietary interventions and/or maintenance of weight loss following one or more dietary interventions in a subject population. By this is meant that a particular nucleotide or nucleotide sequence at the polymorphic site is correlated with said weight loss and/or maintenance.

The polymorphic site may be one which has an association with an improvement in glycemic control attainable by applying one or more dietary interventions in a subject population. By this is meant that a particular nucleotide or nucleotide sequence at the polymorphic site is correlated with said improvement in glycemic control.

The polymorphic position genetically linked to miR-486 may be one or more of the SNPs identified in Table 1 and/or Table 2.

Accordingly, the present methods may comprise determining the nucleotide of the subject at position 26 of one or more of SEQ ID NO: 3-33.

The present methods may comprise determining the nucleotide of the subject at position 26 of SEQ ID NO: 3 (rs545936), wherein the presence of G at position 26 of SEQ ID NO: 3 is indicative that the subject is predicted to lose more weight following the application of one or more dietary interventions and/or that the subject is predicted to better maintain weight loss and/or that the subject is predicted to better improve glycemic control following the application of one or more dietary interventions to the subject.

The present methods may comprise determining the nucleotide of the subject at position 26 of SEQ ID NO: 4 (rs6981587), wherein the presence of C at position 26 of SEQ ID NO: 4 is indicative that the subject is predicted to lose more weight following the application of one or more dietary interventions and/or that the subject is predicted to better maintain weight loss and/or that the subject is predicted to better improve glycemic control following the application of one or more dietary interventions to the subject.

The present methods may comprise determining the nucleotide of the subject at position 26 of SEQ ID NO: 5 (rs190249167), wherein the presence of C at position 26 of SEQ ID NO: 5 is indicative that the subject is predicted to lose more weight following the application of one or more dietary interventions and/or that the subject is predicted to better maintain weight loss and/or that the subject is predicted to better improve glycemic control following the application of one or more dietary interventions to the subject and/or that the subject is predicted to have higher mir-486 levels.

The present methods may comprise determining the nucleotide of the subject at position 26 of SEQ ID NO: 6 (rs56306962), wherein the presence of C at position 26 of SEQ ID NO: 6 is indicative that the subject is predicted to lose more weight following the application of one or more dietary interventions and/or that the subject is predicted to better maintain weight loss and/or that the subject is predicted to better improve glycemic control following the application of one or more dietary interventions to the subject.

The present methods may comprise determining the nucleotide of the subject at position 26 of SEQ ID NO: 7 (rs518629), wherein the presence of T at position 26 of SEQ ID NO: 7 is indicative that the subject is predicted to lose more weight following the application of one or more dietary interventions and/or that the subject is predicted to better maintain weight loss and/or that the subject is predicted to better improve glycemic control following the application of one or more dietary interventions to the subject.

The present methods may comprise determining the nucleotide of the subject at position 26 of SEQ ID NO: 8 (rs77072645), wherein the presence of G at position 26 of SEQ ID NO: 8 is indicative that the subject is predicted to lose more weight following the application of one or more dietary interventions and/or that the subject is predicted to better maintain weight loss and/or that the subject is predicted to better improve glycemic control following the application of one or more dietary interventions to the subject.

The present methods may comprise determining the nucleotide of the subject at position 26 of SEQ ID NO: 9 (rs486499), wherein the presence of G at position 26 of SEQ ID NO: 9 is indicative that the subject is predicted to lose more weight following the application of one or more dietary interventions and/or that the subject is predicted to better maintain weight loss and/or that the subject is predicted to better improve glycemic control following the application of one or more dietary interventions to the subject.

The present methods may comprise determining the nucleotide of the subject at position 26 of SEQ ID NO: 10 (rs554340), wherein the presence of C at position 26 of SEQ ID NO: 10 is indicative that the subject is predicted to lose more weight following the application of one or more dietary interventions and/or that the subject is predicted to better maintain weight loss and/or that the subject is predicted to better improve glycemic control following the application of one or more dietary interventions to the subject.

The present methods may comprise determining the nucleotide of the subject at position 26 of SEQ ID NO: 11 (rs519619), wherein the presence of A at position 26 of SEQ ID NO: 11 is indicative that the subject is predicted to lose more weight following the application of one or more dietary interventions and/or that the subject is predicted to better maintain weight loss and/or that the subject is predicted to better improve glycemic control following the application of one or more dietary interventions to the subject.

The present methods may comprise determining the nucleotide of the subject at position 26 of SEQ ID NO: 12 (rs11996576), wherein the presence of G at position 26 of SEQ ID NO: 12 is indicative that the subject is predicted to lose more weight following the application of one or more dietary interventions and/or that the subject is predicted to better maintain weight loss and/or that the subject is predicted to better improve glycemic control following the application of one or more dietary interventions to the subject.

The present methods may comprise determining the nucleotide of the subject at position 26 of SEQ ID NO: 13 (rs3736217), wherein the presence of G at position 26 of SEQ ID NO: 13 is indicative that the subject is predicted to lose more weight following the application of one or more dietary interventions and/or that the subject is predicted to better maintain weight loss and/or that the subject is predicted to better improve glycemic control following the application of one or more dietary interventions to the subject.

The present methods may comprise determining the nucleotide of the subject at position 26 of SEQ ID NO: 14 (rs6983305), wherein the presence of T at position 26 of SEQ ID NO: 14 is indicative that the subject is predicted to lose more weight following the application of one or more dietary interventions and/or that the subject is predicted to better maintain weight loss and/or that the subject is predicted to better improve glycemic control following the application of one or more dietary interventions to the subject.

The present methods may comprise determining the nucleotide of the subject at position 26 of SEQ ID NO: 15 (rs55794933), wherein the presence of A at position 26 of SEQ ID NO: 15 is indicative that the subject is predicted to lose more weight following the application of one or more dietary interventions and/or that the subject is predicted to better maintain weight loss and/or that the subject is predicted to better improve glycemic control following the application of one or more dietary interventions to the subject and/or that the subject is predicted to have higher mir-486 levels.

The present methods may comprise determining the nucleotide of the subject at position 26 of SEQ ID NO: 16 (rs72638941), wherein the presence of C at position 26 of SEQ ID NO: 16 is indicative that the subject is predicted to lose more weight following the application of one or more dietary interventions and/or that the subject is predicted to better maintain weight loss and/or that the subject is predicted to better improve glycemic control following the application of one or more dietary interventions to the subject and/or that the subject is predicted to have higher mir-486 levels.

The present methods may comprise determining the nucleotide of the subject at position 26 of SEQ ID NO: 17 (rs72638952), wherein the presence of G at position 26 of SEQ ID NO: 17 is indicative that the subject is predicted to lose more weight following the application of one or more dietary interventions and/or that the subject is predicted to better maintain weight loss and/or that the subject is predicted to better improve glycemic control following the application of one or more dietary interventions to the subject and/or that the subject is predicted to have higher mir-486 levels.

The present methods may comprise determining the nucleotide of the subject at position 26 of SEQ ID NO: 18 (rs72638939), wherein the presence of C at position 26 of SEQ ID NO: 18 is indicative that the subject is predicted to lose more weight following the application of one or more dietary interventions and/or that the subject is predicted to better maintain weight loss and/or that the subject is predicted to better improve glycemic control following the application of one or more dietary interventions to the subject and/or that the subject is predicted to have higher mir-486 levels.

The present methods may comprise determining the nucleotide of the subject at position 26 of SEQ ID NO: 19 (rs72638940), wherein the presence of A at position 26 of SEQ ID NO: 19 is indicative that the subject is predicted to lose more weight following the application of one or more dietary interventions and/or that the subject is predicted to better maintain weight loss and/or that the subject is predicted to better improve glycemic control following the application of one or more dietary interventions to the subject and/or that the subject is predicted to have higher mir-486 levels.

The present methods may comprise determining the nucleotide of the subject at position 26 of SEQ ID NO: 20 (rs117956059), wherein the presence of C at position 26 of SEQ ID NO: 20 is indicative that the subject is predicted to lose more weight following the application of one or more dietary interventions and/or that the subject is predicted to better maintain weight loss and/or that the subject is predicted to better improve glycemic control following the application of one or more dietary interventions to the subject and/or that the subject is predicted to have higher mir-486 levels.

The present methods may comprise determining the nucleotide of the subject at position 26 of SEQ ID NO: 21 (rs72638943), wherein the presence of T at position 26 of SEQ ID NO: 21 is indicative that the subject is predicted to lose more weight following the application of one or more dietary interventions and/or that the subject is predicted to better maintain weight loss and/or that the subject is predicted to better improve glycemic control following the application of one or more dietary interventions to the subject and/or that the subject is predicted to have higher mir-486 levels.

The present methods may comprise determining the nucleotide of the subject at position 26 of SEQ ID NO: 22 (rs72638944), wherein the presence of G at position 26 of SEQ ID NO: 22 is indicative that the subject is predicted to lose more weight following the application of one or more dietary interventions and/or that the subject is predicted to better maintain weight loss and/or that the subject is predicted to better improve glycemic control following the application of one or more dietary interventions to the subject and/or that the subject is predicted to have higher mir-486 levels.

The present methods may comprise determining the nucleotide of the subject at position 26 of SEQ ID NO: 23 (rs72638945), wherein the presence of C at position 26 of SEQ ID NO: 23 is indicative that the subject is predicted to lose more weight following the application of one or more dietary interventions and/or that the subject is predicted to better maintain weight loss and/or that the subject is predicted to better improve glycemic control following the application of one or more dietary interventions to the subject and/or that the subject is predicted to have higher mir-486 levels.

The present methods may comprise determining the nucleotide of the subject at position 26 of SEQ ID NO: 24 (rs72638947), wherein the presence of C at position 26 of SEQ ID NO: 24 is indicative that the subject is predicted to lose more weight following the application of one or more dietary interventions and/or that the subject is predicted to better maintain weight loss and/or that the subject is predicted to better improve glycemic control following the application of one or more dietary interventions to the subject and/or that the subject is predicted to have higher mir-486 levels.

The present methods may comprise determining the nucleotide of the subject at position 26 of SEQ ID NO: 25 (rs72638950), wherein the presence of A at position 26 of SEQ ID NO: 25 is indicative that the subject is predicted to lose more weight following the application of one or more dietary interventions and/or that the subject is predicted to better maintain weight loss and/or that the subject is predicted to better improve glycemic control following the application of one or more dietary interventions to the subject and/or that the subject is predicted to have higher mir-486 levels.

The present methods may comprise determining the nucleotide of the subject at position 26 of SEQ ID NO: 26 (rs78673930), wherein the presence of A at position 26 of SEQ ID NO: 26 is indicative that the subject is predicted to lose more weight following the application of one or more dietary interventions and/or that the subject is predicted to better maintain weight loss and/or that the subject is predicted to better improve glycemic control following the application of one or more dietary interventions to the subject and/or that the subject is predicted to have higher mir-486 levels.

The present methods may comprise determining the nucleotide of the subject at position 26 of SEQ ID NO: 27 (rs139183594), wherein the presence of T at position 26 of SEQ ID NO: 27 is indicative that the subject is predicted to lose more weight following the application of one or more dietary interventions and/or that the subject is predicted to better maintain weight loss and/or that the subject is predicted to better improve glycemic control following the application of one or more dietary interventions to the subject and/or that the subject is predicted to have higher mir-486 levels.

The present methods may comprise determining the nucleotide of the subject at position 26 of SEQ ID NO: 28 (rs77385495), wherein the presence of T at position 26 of SEQ ID NO: 28 is indicative that the subject is predicted to lose more weight following the application of one or more dietary interventions and/or that the subject is predicted to better maintain weight loss and/or that the subject is predicted to better improve glycemic control following the application of one or more dietary interventions to the subject and/or that the subject is predicted to have higher mir-486 levels.

The present methods may comprise determining the nucleotide of the subject at position 26 of SEQ ID NO: 29 (rs117135799), wherein the presence of T at position 26 of SEQ ID NO: 29 is indicative that the subject is predicted to lose more weight following the application of one or more dietary interventions and/or that the subject is predicted to better maintain weight loss and/or that the subject is predicted to better improve glycemic control following the application of one or more dietary interventions to the subject and/or that the subject is predicted to have higher mir-486 levels.

The present methods may comprise determining the nucleotide of the subject at position 26 of SEQ ID NO: 30 (rs117308321), wherein the presence of A at position 26 of SEQ ID NO: 30 is indicative that the subject is predicted to lose more weight following the application of one or more dietary interventions and/or that the subject is predicted to better maintain weight loss and/or that the subject is predicted to better improve glycemic control following the application of one or more dietary interventions to the subject and/or that the subject is predicted to have higher mir-486 levels.

The present methods may comprise determining the nucleotide of the subject at position 26 of SEQ ID NO: 31 (rs76356889), wherein the presence of T at position 26 of SEQ ID NO: 31 is indicative that the subject is predicted to lose more weight following the application of one or more dietary interventions and/or that the subject is predicted to better maintain weight loss and/or that the subject is predicted to better improve glycemic control following the application of one or more dietary interventions to the subject and/or that the subject is predicted to have higher mir-486 levels.

The present methods may comprise determining the nucleotide of the subject at position 26 of SEQ ID NO: 32 (rs80105613), wherein the presence of T at position 26 of SEQ ID NO: 32 is indicative that the subject is predicted to lose more weight following the application of one or more dietary interventions and/or that the subject is predicted to better maintain weight loss and/or that the subject is predicted to better improve glycemic control following the application of one or more dietary interventions to the subject and/or that the subject is predicted to have higher mir-486 levels.

The present methods may comprise determining the nucleotide of the subject at position 26 of SEQ ID NO: 33 (rs116964396), wherein the presence of A at position 26 of SEQ ID NO: 33 is indicative that the subject is predicted to lose more weight following the application of one or more dietary interventions and/or that the subject is predicted to better maintain weight loss and/or that the subject is predicted to better improve glycemic control following the application of one or more dietary interventions to the subject and/or that the subject is predicted to have higher mir-486 levels.

By "X at position 26" referred to above (wherein "X" is the identified nucleotide at position 26 for each of SEQ ID NO: 3-33, respectively) it is meant that the subject has at least one copy of X at said site, i.e., the subject may have the genotype X/X (homozygous) or X/Y (heterozygous), wherein Y is any nucleotide other than X.

For example, by "G at position 26 of SEQ ID NO: 3" it is meant that the subject has at least one copy of G at said site, i.e., the subject may have the genotype G/G (homozygous) or G/Y (heterozygous), wherein Y is any nucleotide other than G.

It should be noted that in this application, SNPs are referred to by, for example, reference to a position in SEQ ID NO: 3-33 (e.g. position 26). However, when such references are made, it will be understood that the invention is not to be limited to the exact sequence as set out in the SEQ ID NO but includes variants and derivatives thereof. Instead, identification of SNP locations in similar sequences are contemplated (i.e. SNPs at positions which the skilled person would consider correspond to the positions identified in the SEQ ID numbers). The person skilled in the art can readily align similar sequences and locate the same SNP locations.

It should further be noted that detection of the nucleotide in the complement strand to SEQ ID NO: 3-33 base-pairs with the nucleotide at position 26 of SEQ ID NO: 3-33 is of course within the scope of the claimed invention.

The term "one or more polymorphic positions" as used herein may include at least one, at least two, at least three, at least four, at least five, at least six, at least seven, at least eight, at least nine, at least ten, at least fifteen, at least twenty, at least twenty-five or at least thirty or all of the polymorphic positions as described herein.

In one embodiment, the one or more polymorphic positions are selected from: (i) position 26 of SEQ ID NO: 3 (rs545936); (ii) position 26 of SEQ ID NO: 4 (rs6981587) and (iii) position 26 of SEQ ID NO: 5 (rs190249167).

Preferably the method comprises determining the presence of G or A at position 26 of SEQ ID NO: 3; and/or T or C at position 26 of SEQ ID NO: 4; and/or T or C at position 26 of SEQ ID NO: 5.

In one embodiment, the present method may comprise determining the presence of G at position 26 of SEQ ID NO: 3; and/or C at position 26 of SEQ ID NO: 4; and/or C at position 26 of SEQ ID NO: 5.

It will be apparent to the person skilled in the art that if a subject does not have the nucleotide(s) at position 26 of any one of SEQ ID NO: 3-33 as identified above, this may be indicative that the subject, with respect to subjects with the nucleotide(s), is predicted to lose less weight following the application of one or more dietary interventions and/or that the subject is predicted to have maintenance of weight loss and/or that the subject is predicted to have lesser improvement of glycemic control following the application of one or more dietary interventions to the subject.

It will be apparent to the person skilled in the art that there are a large number of analytical procedures which may be used to detect the presence or absence of variant nucleotides at one or more polymorphic positions of the invention. In general, the detection of allelic variation requires a mutation discrimination technique, optionally an amplification reaction and optionally a signal generation system.

Detection of Alleles

The nucleic acids obtained from the sample can be genotyped to identify the particular allele present for a marker locus. A sample of sufficient quantity to permit direct detection of marker alleles from the sample may be obtained.

Alternatively, a smaller sample is obtained from the subject and the nucleic acids are amplified prior to detection. Optionally, the nucleic acid sample is purified (or partially purified) prior to detection of the marker alleles.

Examples of allele detection methods are given below:

Allele Specific PCR

Allele-specific PCR differentiates between target regions differing in the presence of absence of a variation or polymorphism. PCR amplification primers are chosen based upon their complementarity to the target sequence, such as a sequence disclosed herein. The primers bind only to certain alleles of the target sequence.

Allele Specific Oligonucleotide Screening Methods

Further screening methods employ the allele-specific oligonucleotide (ASO) screening methods (e.g. see Saiki et al., Nature 324:163-166, 1986).

Oligonucleotides with one or more base pair mismatches are generated for any particular allele. ASO screening methods detect mismatches between one allele in the target genomic or PCR amplified DNA and the other allele, showing decreased binding of the oligonucleotide relative to the second allele (i.e. the other allele) oligonucleotide. Oligonucleotide probes can be designed that under low stringency will bind to both polymorphic forms of the allele, but which at high stringency, bind to the allele to which they correspond. Alternatively, stringency conditions can be devised in which an essentially binary response is obtained, i.e., an ASO corresponding to a variant form of the target gene will hybridize to that allele, and not to the wildtype allele.

Ligase Mediated Allele Detection Method

Ligase can also be used to detect point mutations, such as the SNPs in a ligation amplification reaction (e.g. as described in Wu et al., Genomics 4:560-569, 1989). The ligation amplification reaction (LAR) utilizes amplification of specific DNA sequence using sequential rounds of template dependent ligation (e.g. as described in Wu, supra, and Barany, Proc. Nat. Acad. Sci. 88:189-193, 1990).

Denaturing Gradient Gel Electrophoresis

Amplification products generated using the polymerase chain reaction can be analyzed by the use of denaturing gradient gel electrophoresis. Different alleles can be identified based on the different sequence-dependent melting properties and electrophoretic migration of DNA in solution. DNA molecules melt in segments, termed melting domains, under conditions of increased temperature or denaturation.

Each melting domain melts cooperatively at a distinct, base-specific melting temperature (Tm). Melting domains are at least 20 base pairs in length, and can be up to several hundred base pairs in length.

Differentiation between alleles based on sequence specific melting domain differences can be assessed using polyacrylamide gel electrophoresis, as described in Chapter 7 of Erlich, ed., PCR Technology, Principles and Applications for DNA Amplification, W. H. Freeman and Co., New York (1992).

Generally, a target region to be analyzed by denaturing gradient gel electrophoresis is amplified using PCR primers flanking the target region. The amplified PCR product is applied to a polyacrylamide gel with a linear denaturing gradient as described in Myers et al., Meth. Enzymol. 155:501-527, 1986, and Myers et al., in Genomic Analysis, A Practical Approach, K. Davies Ed. IRL Press Limited, Oxford, pp. 95 139, 1988. The electrophoresis system is maintained at a temperature slightly below the Tm of the melting domains of the target sequences.

In an alternative method of denaturing gradient gel electrophoresis, the target sequences can be initially attached to a stretch of GC nucleotides, termed a GC clamp, as described in Chapter 7 of Erlich, supra. In one example, at least 80% of the nucleotides in the GC clamp are either guanine or cytosine. In another example, the GC clamp is at least 30 bases long. This method is particularly suited to target sequences with high Tm's.

Generally, the target region is amplified by the polymerase chain reaction as described above. One of the oligonucleotide PCR primers carries at its 5' end, the GC clamp region, at least 30 bases of the GC rich sequence, which is incorporated into the 5' end of the target region during amplification. The resulting amplified target region is run on an electrophoresis gel under denaturing gradient conditions as described above. DNA fragments differing by a single base change will migrate through the gel to different positions, which can be visualized by ethidium bromide staining.

Temperature Gradient Gel Electrophoresis

Temperature gradient gel electrophoresis (TGGE) is based on the same underlying principles as denaturing gradient gel electrophoresis, except the denaturing gradient is produced by differences in temperature instead of differences in the concentration of a chemical denaturant. Standard TGGE utilizes an electrophoresis apparatus with a temperature gradient running along the electrophoresis path. As samples migrate through a gel with a uniform concentration of a chemical denaturant, they encounter increasing temperatures. An alternative method of TGGE, temporal temperature gradient gel electrophoresis (TTGE or tTGGE) uses a steadily increasing temperature of the entire electrophoresis gel to achieve the same result. As the samples migrate through the gel the temperature of the entire gel increases, leading the samples to encounter increasing temperature as they migrate through the gel. Preparation of samples, including PCR amplification with incorporation of a GC clamp, and visualization of products are the same as for denaturing gradient gel electrophoresis.

Single-Strand Conformation Polymorphism Analysis

Target sequences or alleles can be differentiated using single-strand conformation polymorphism analysis, which identifies base differences by alteration in electrophoretic migration of single stranded PCR products, for example as described in Orita et al., Proc. Nat. Acad. Sci. 85:2766-2770, 1989. Amplified PCR products can be generated as described above, and heated or otherwise denatured, to form single stranded amplification products. Single-stranded nucleic acids can refold or form secondary structures which are partially dependent on the base sequence. Thus, electrophoretic mobility of single-stranded amplification products can detect base-sequence difference between alleles or target sequences.

Chemical or Enzymatic Cleavage of Mismatches

Differences between target sequences can also be detected by differential chemical cleavage of mismatched base pairs, for example as described in Grompe et al., Am. J. Hum. Genet. 48:212-222, 1991. In another method, differences between target sequences can be detected by enzymatic cleavage of mismatched base pairs, as described in Nelson et al., Nature Genetics 4:11-18, 1993. Briefly, genetic material from an animal and an affected family member can be used to generate mismatch free heterohybrid DNA duplexes. As used herein, 'heterohybrid' means a DNA duplex strand comprising one strand of DNA from one animal, and a second DNA strand from another animal, usually an animal differing in the phenotype for the trait of interest.

Non-Gel Systems

Other possible techniques include non-gel systems such as TaqMan™ (Perkin Elmer). In this system oligonucleotide PCR primers are designed that flank the mutation in question and allow PCR amplification of the region. A third oligonucleotide probe is then designed to hybridize to the region containing the base subject to change between different alleles of the gene. This probe is labeled with fluorescent dyes at both the 5' and 3' ends. These dyes are chosen such that while in this proximity to each other the fluorescence of one of them is quenched by the other and cannot be detected. Extension by Taq DNA polymerase from the PCR primer positioned 5' on the template relative to the probe leads to the cleavage of the dye attached to the 5' end of the annealed probe through the 5' nuclease activity of the Taq DNA polymerase. This removes the quenching effect allowing detection of the fluorescence from the dye at the 3' end of the probe. The discrimination between different DNA sequences arises through the fact that if the hybridization of the probe to the template molecule is not complete, i.e. there is a mismatch of some form, the cleavage of the dye does not take place. Thus only if the nucleotide sequence of the oligonucleotide probe is completely complimentary to the template molecule to which it is bound will quenching be removed. A reaction mix can contain two different probe sequences each designed against different alleles that might be present thus allowing the detection of both alleles in one reaction.

Many current methods for the detection of allelic variation are reviewed by Nollau et ah, Clin. Chem. 43, 1114-1120, 1997; and in standard textbooks, for example "Laboratory Protocols for Mutation Detection", Ed. by U. Landegren, Oxford University Press, 1996 and "PCR", 2nd Edition by Newton & Graham, BIOS Scientific Publishers Limited, 1997.

Combinations of Biomarkers

Whilst individual biomarkers may have predictive value in the methods of the present invention, the quality and/or the predictive power of the methods may be improved by combining values from multiple biomarkers.

For example the present methods may comprise determining the nucleotide of the subject at one or more polymorphic positions as described herein.

The present methods may comprise combining miR-486 levels with determining the nucleotide of the subject at one or more polymorphic positions as described herein.

Determining the Level of One or More Biomarkers in the Sample

In one embodiment, the level of one or more biomarkers is determined prior to the dietary intervention. In another embodiment, the level of one or more biomarkers is determined prior to, and after the dietary intervention. The biomarker level may also be determined at predetermined times throughout the dietary intervention. These predetermined times may be periodic throughout the dietary intervention, e.g. every day or three days, or may depend on the subject being tested, the type of sample being analysed and/or the degree of weight loss which is predicted to be attained.

When obtained prior to the dietary intervention, the biomarker level may be termed the "fasting level". When obtained after the dietary intervention, the biomarker level may be termed the "calorie intake level". For example, the biomarker level may be determined at fasting, or at fasting and after calorie intake. Most preferably the fasting level of each biomarker is determined.

In one embodiment, the biomarker level is compared with a reference value. In which case, the biomarker level in the sample and the reference value are determined using the same analytical method.

Comparison to a Reference or Control

The present method may further comprise a step of comparing the level the biomarker (e.g. miR-486) in the test sample to one or more reference or control values. The reference value may be associated with a pre-defined ability of a subject to lose weight and/or improve glycemic control following dietary intervention. In some embodiments, the reference value is a value obtained previously for a subject or group of subjects following a certain dietary intervention. The reference value may be based on an average level, e.g. a mean or median level, from a group of subjects following the dietary intervention.

Combining the Biomarker Levels with Anthropometric Measures and/or Lifestyle Characteristics In one embodiment, the present method further comprises combining the level of miR-486 and/or the determination of the genotype as referred to herein (e.g., determining the presence of a polymorphic marker e.g., SNP as described herein) with one or more anthropometric measures and/or lifestyle characteristics of the subject. By combining this information, an improved predictive model is provided for the degree of weight loss and/or improvement in glycemic control attainable by a subject.

As is known in the art, an anthropometric measure is a measurement of a subject. In one embodiment, the anthropometric measure is selected from the group consisting of gender, age (in years), weight (in kilograms), height (in centimetres), body fat composition (in kilograms), and body mass index (in $kg/m^2$). Other anthropometric measures will also be known to the skilled person in the art.

By the term "lifestyle characteristic" is meant any lifestyle choice made by a subject, this includes all dietary intake data, activity measures or data from questionnaires of lifestyle, motivation or preferences. In one embodiment, the lifestyle characteristic is whether the subject is a smoker or a non-smoker. This is also referred to herein as the smoking status of the subject.

In a preferred embodiment, the level of miR-486 and/or the determination of the genotype as referred to herein (e.g., determining the presence of a polymorphic marker e.g., SNP as described herein) are determined for a sample from the subject and these levels are combined with the gender, age, smoking status and body mass index of the subject in order to predict the weight loss and/or improvement in glycemic control attainable by the subject. Preferably the degree of weight loss is represented by the body mass index that a subject is predicted to attain by applying the dietary intervention.

In one embodiment, the subject is of European ancestry.

Subject Stratification

The degree of weight loss and/or improvement in glycemic control predicted by the method of the present invention may also be compared to one or more pre-determined thresholds. Using such thresholds, subjects may be stratified into categories which are indicative of the degree of predicted weight loss and/or improvement in glycemic control, e.g. low, medium, high and/or very high predicted degree of weight loss and/or improvement in glycemic control. The extent of the divergence from the thresholds is useful to determine which subjects would benefit most from certain interventions. In this way, dietary intervention and modification of lifestyle can be optimised, and realistic expectations of the weight loss and/or improvement in glycemic control to be achieved by the subject can be set.

In one embodiment, the categories include weight loss resistant subjects and weight loss sensitive subjects.

By the term "weight loss resistant" is meant a predicted degree of weight loss which is less than a predetermined value. Preferably "weight loss resistant" is defined as a subject having a weight loss percentage inferior to a predetermined value e.g. a subject predicted to lose less weight than the $10^{th}$, $15^{th}$, $20^{th}$ or $30^{th}$ percentile of the expected weight loss for the subject.

Preferably the degree of weight loss is represented by the number of BMI units lost, where BMI loss=((BMI1−BMI2)*100)/BMI1, wherein BMI1 is the body mass index of the subject before the dietary intervention and BMI2 is the predicted body mass index of the subject after the dietary intervention.

By the term "weight loss sensitive" is meant a predicted degree of weight loss of more than a predetermined value. Preferably "weight loss sensitive" is defined as a subject having a weight loss percentage superior to a predetermined threshold value. For example a subject predicted to lose more weight than the $85^{th}$, $80^{th}$ or $75^{th}$ percentile of the expected weight loss.

The "expected weight loss" can be obtained from data of a population of subjects that have undergone the same dietary intervention as the one being tested.

In another embodiment, subjects may be stratified into categories "weight loss sensitive" or "weight loss resistant" which are indicative of the risk reduction of the subject for obesity or obesity-related disorders, e.g. low, medium, high and/or very high risk reduction. Low, medium and high-risk reduction groups may be defined in terms of absolute weight loss, where the absolute weight loss relates to clinical criteria for obesity or a particular obesity-related disorder.

For example, if the aim is to reduce the risk for type 2 diabetes in an obese individual, "very high risk reduction" may be defined as those predicted to lose at least 10% body weight after the dietary intervention. This is in accordance with the criteria set out in Part II of the World Health Organ Tech Rep Ser. 2000; 894:i-xii, 1-253). Moreover every 1% reduction in body weight of an obese person leads to a fall in systolic and diastolic blood pressure, and fall in low-density lipoprotein cholesterol, hence reduces the risk of cardio-vascular disease and dyslipidaemia respectively.

In one embodiment, the categories include glycemic control resistant subjects and glycemic control sensitive subjects.

By the term "glycemic control resistant" is meant a predicted degree of improvement in glycemic control which is less than a predetermined value. Preferably "glycemic control resistant" is defined as a subject having a percentage improvement in glycemic control inferior to a predetermined value e.g. a subject predicted to improve in glycemic control by less than the 10th, 15th, 20th or 30th percentile of the expected improvement in glycemic control for the subject.

Preferably the degree of improvement in glycemic control is represented by the change in a glycemic control measurement as described herein, where glycemic control improvement=((GC1−GC2)*100)/GC1, wherein GC1 is the glycemic control measurement of the subject before the dietary intervention and GC2 is the glycemic control measurement of the subject after the dietary intervention.

By the term "glycemic control sensitive" is meant a predicted degree of improvement in glycemic control of more than a predetermined value. Preferably "glycemic control sensitive" is defined as a subject having a percentage improvement in glycemic control superior to a predetermined threshold value. For example a subject predicted to improve in glycemic control by more than the 85th, 80th or 75th percentile of the expected improvement in glycemic control.

The "expected improvement in glycemic control" can be obtained from data of a population of subjects that have undergone the same dietary intervention as the one being tested.

In another embodiment, subjects may be stratified into categories "glycemic control sensitive" or "glycemic control resistant" which are indicative of the risk reduction of the subject for obesity or obesity-related disorders, e.g. low, medium, high and/or very high risk reduction. Low, medium and high risk reduction groups may be defined in terms of absolute weight loss, where the absolute weight loss relates to clinical criteria for obesity or a particular obesity-related disorder.

For example, if the aim is to reduce the risk for type 2 diabetes in an obese individual, "very high risk reduction" may be defined as those predicted to lose at least 10% body weight after the dietary intervention. This is in accordance with the criteria set out in Part II of the World Health Organ Tech Rep Ser. 2000; 894:i-xii, 1-253). Moreover every 1% reduction in body weight of an obese person leads to a fall in systolic and diastolic blood pressure, and fall in low-density lipoprotein cholesterol, hence reduces the risk of cardio-vascular disease and dyslipidaemia respectively.

Method for Selecting a Modification of Lifestyle of a Subject

In a further aspect, the present invention provides a method for modifying the lifestyle of a subject. The modification in lifestyle in the subject may be any change as described herein, e.g. a change in diet, more exercise, a different working and/or living environment etc.

Preferably the modification is a dietary intervention as described herein. More preferably the dietary intervention includes the administration of at least one diet product. The diet product preferably has not previously been consumed or was consumed in different amounts by the subject. The diet product may be as described herein. Modifying a lifestyle of the subject also includes indicating a need for the subject to change his/her lifestyle, e.g. prescribing more exercise or stopping smoking.

For example, if a subject is not predicted to lose weight and/or improve glycemic control on a low calorie diet, a modification may include more exercise in the subject's lifestyle.

Use of Diet Products

In one aspect, the present invention provides a diet product for use as part of a low calorie diet for weight loss. The diet product being administered to a subject that is predicted to attain a degree of weight loss, weight maintenance and/or a degree of improvement in glycemic control by the methods described herein.

In another aspect, the present invention provides a diet product for use in treating obesity or an obesity-related disorder, wherein the diet product is administered to a subject that is predicted to attain a degree of weight loss, weight maintenance and/or a degree of improvement in glycemic control by the methods described herein.

The obesity-related disorder may be selected from the group consisting of diabetes (e.g. type 2 diabetes), stroke, high cholesterol, cardiovascular disease, insulin resistance, coronary heart disease, metabolic syndrome, hypertension and fatty liver. In a further aspect, the present invention provides the use of a diet product in a low calorie diet for weight loss where the diet product is administered to a subject that is predicted to attain a degree of weight loss, weight maintenance and/or a degree of improvement in glycemic control by the methods described herein.

Primers/Probes

According to one aspect of the present invention there is provided an allele-specific oligonucleotide primer or an allele-specific oligonucleotide probe capable of detecting a polymorphism at a polymorphic position as described herein (e.g. as shown in Table 1 or Table 2).

According to another aspect of the present invention there is provided an allele-specific oligonucleotide primer or an allele-specific oligonucleotide probe capable of detecting a polymorphic position selected from:

(i) position 26 of SEQ ID NO: 3 (rs545936)
(ii) position 26 of SEQ ID NO: 4 (rs6981587) or
(iii) position 26 of SEQ ID NO: 5 (rs190249167).

It should be noted that reference to an allele-specific oligonucleotide primer or an allele-specific oligonucleotide probe which is capable of detecting a polymorphic position as described herein includes an allele-specific oligonucleotide primer or an allele-specific oligonucleotide probe which is capable of detecting the compliment of a polymorphism as described herein (e.g. as shown in Table 1 or Table 2).

For example, an allele-specific oligonucleotide primer or an allele-specific oligonucleotide probe which is capable of detecting a polymorphic position selected position 26 of SEQ ID NO: 3; position 26 of SEQ ID NO: 4 or position 26 of SEQ ID NO: 5, includes an allele-specific oligonucleotide primer or an allele-specific oligonucleotide probe which is capable of detecting the compliment of each of these positions, respectively.

The present invention further provides an allele-specific oligonucleotide primer capable of detecting a polymorphism at a polymorphic position as described herein (e.g. as shown in Table 1 or Table 2) for use in identifying a subject predicted to achieve a degree of weight loss and/or a degree of maintenance of weight loss and/or a degree of improvement in glycemic control following one or more dietary interventions.

The present invention further provides an allele-specific oligonucleotide probe capable of detecting a polymorphism at a polymorphic position as described herein (e.g. as shown in Table 1 or Table 2) for use in identifying a subject predicted to achieve a degree of weight loss and/or a degree of maintenance of weight loss and/or a degree of improvement in glycemic control following one or more dietary interventions.

The allele-specific primers of the present invention are used, generally together with a constant primer, in an amplification reaction such as a PCR reaction, which provides the discrimination between alleles through selective amplification of one allele at a particular sequence position e.g. as used for ARMS(TM) assays. The allele-specific primers of the present invention are preferably 15-50 nucleotides, more preferably about 15-35 nucleotides, still more preferably about 17-30 nucleotides.

Primers may be manufactured using any convenient method of synthesis. Examples of such methods may be found in standard textbooks, for example "Protocols for Oligonucleotides and Analogues; Synthesis and Properties," Methods in Molecular Biology Series; Volume 20; Ed. Sudhir Agrawal, Humana ISBN: 0-89603-247-7; 1993; 1st Edition. If required the primer(s) may be labelled to facilitate detection.

The design of probes will be apparent to the molecular biologist of ordinary skill. Such probes are of any convenient length such as, for example, up to 100 bases, up to 50 bases, up to 40 bases and up to 30 bases in length. For example, the probes may be 10 to 30 bases, preferably 18-30 bases in length. The probes may comprise base sequences entirely complementary to the target sequence. However, if required one or more mismatches may be introduced, provided that the discriminatory power of the oligonucleotide probe is not unduly affected. The probes of the invention may carry one or more labels to facilitate detection.

An allele-specific probe capable of detecting a polymorphism at a polymorphic position as described herein may discriminate, in a hybridisation reaction, between a sequence comprising base shown as the "Ref allele" in Table 1 or Table 2 at position 26 each of SEQ IDs NO:3-36, respectively (or a sequence complementary to such a gene or fragment), and sequence comprising a different base at position 26 of each of SEQ IDs NO: 3-36, respectively (or a sequence or fragment complementary to such a gene or fragment).

For example, an allele-specific probe capable of detecting a polymorphism at position 26 of SEQ ID NO: 3 may discriminate, in a hybridisation reaction, between a sequence comprising base A at position 101 of SEQ ID NO: 3 (or a sequence complementary to such a gene or fragment), and sequence comprising base G at position 26 of SEQ ID NO: 3 (or a sequence or fragment complementary to such a gene or fragment).

The primers and/or probes of the present invention will typically be in the form of nucleic acids (e.g. DNA or cDNA). Alternatively, the primers and/or probes may be in the form of nucleic acid analogues, for example PNA (Peptide Nucleic Acids), LNA (Locked Nucleic Acids) or BNA (Bridged Nucleic Acids). The primers or probes may be nucleic acids which have been substituted in part by LNA or PNA.

Primer Design Strategy

Increased use of polymerase chain reaction (PCR) methods has stimulated the development of many programs to aid in the design or selection of oligonucleotides used as primers for PCR. Four examples of such programs that are freely available via the Internet are: PRIMER by Mark Daly and Steve Lincoln of the Whitehead Institute (UNIX, VMS, DOS, and Macintosh), Oligonucleotide Selection Program (OSP) by Phil Green and LaDeana Hiller of Washington University in St. Louis (UNIX, VMS, DOS, and Macintosh), PGEN by Yoshi (DOS only), and Amplify by Bill Engels of the University of Wisconsin (Macintosh only).

Generally these programs help in the design of PCR primers by searching for bits of known repeated-sequence elements and then optimizing the Tm by analyzing the length and GC content of a putative primer. Commercial software is also available 35 and primer selection procedures are rapidly being included in most general sequence analysis packages.

Designing oligonucleotides for use primers requires selection of an appropriate sequence that specifically recognizes the target, and then testing the sequence to eliminate the possibility that the oligonucleotide will have a stable secondary structure. Inverted repeats in the sequence can be identified using a repeat-identification or RNA-folding programs.

If a possible stem structure is observed, the sequence of the primer can be shifted a few nucleotides in either direction to minimize the predicted secondary structure.

For PCR primers used to amplify genomic DNA, the primer sequence should be compared to the sequences in the GenBank database to determine if any significant matches occur. If the oligonucleotide sequence is present in any known DNA sequence or, more importantly, in any known repetitive elements, the primer sequence should be changed.

Kits

According to another aspect of the present invention there is provided a diagnostic kit comprising an allele-specific oligonucleotide probe of the invention and/or an allele-specific primer of the invention.

In one embodiment the diagnostic kit comprises two or more allele-specific oligonucleotide primers and/or allele-specific oligonucleotide probes capable of detecting polymorphic positions:

(i) position 26 of SEQ ID NO: 3 (rs545936)
(ii) position 26 of SEQ ID NO: 4 (rs6981587) and/or
(iii) position 26 of SEQ ID NO: 5 (rs190249167).

In one embodiment the diagnostic kit comprises two or more allele-specific oligonucleotide primers and/or allele-specific oligonucleotide probes capable of determining the presence of G at position 26 of SEQ ID NO: 3; and/or C at position 26 of SEQ ID NO: 4; and/or C at position 26 of SEQ ID NO: 5.

The diagnostic kits may comprise appropriate packaging and instructions for use in the methods of the invention. Such kits may further comprise appropriate buffer(s) and polymerase(s) such as thermostable polymerases, for example taq polymerase.

Computer Program Product

The methods described herein may be implemented as a computer program running on general purpose hardware, such as one or more computer processors. In some embodiments, the functionality described herein may be implemented by a device such as a smartphone, a tablet terminal or a personal computer.

In one aspect, the present invention provides a computer program product comprising computer implementable instructions for causing a programmable computer to predict the degree of weight loss based on the levels of biomarkers as described herein.

In another aspect, the present invention provides a computer program product comprising computer implementable instructions for causing a device to predict the degree of weight loss, weight maintenance and/or degree of improvement in glycemic control given the level of miR-486 and/or the determination of the genotype as referred to herein (e.g., determining the presence of a polymorphic marker e.g., SNP as described herein) from the user. Preferably the miR-486 levels are fasting levels. The computer program product may also be given anthropometric measures and/or lifestyle characteristics from the user. As described herein, anthropometric measures include age, weight, height, gender and body mass index and lifestyle characteristics include smoking status.

In one embodiment, the user inputs into the device levels of miR-486 and/or the genotype as referred to herein (e.g., the polymorphic marker e.g., a SNP as described herein), optionally along with age, body mass index, gender and smoking status. The device then processes this information and provides a prediction on the degree of weight loss attainable by the user from a dietary intervention.

The device may generally be a server on a network. However, any device may be used as long as it can process biomarker data and/or anthropometric and lifestyle data using a processor, a central processing unit (CPU) or the like. The device may, for example, be a smartphone, a tablet terminal or a personal computer and output information indicating the degree of weight loss attainable by the user.

Those skilled in the art will understand that they can freely combine all features of the present invention described herein, without departing from the scope of the invention as disclosed.

Various preferred features and embodiments of the present invention will now be described by way of non-limiting examples.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; D. M. J. Lilley and J. E. Dahlberg, 1992, *Methods of Enzymology: DNA Structure Part A: Synthesis and Physical Analysis of DNA* Methods in Enzymology, Academic Press; and E. M. Shevach and W. Strober, 1992 and periodic supplements, *Current Protocols in Immunology*, John Wiley & Sons, New York, N.Y. Each of these general texts is herein incorporated by reference.

EXAMPLES

Example 1—miR-486 SNPs Predict Weight Loss

Following genome-wide association analyses of the Ottawa and Diogenes cohort (two-stage analyses, FDR set at 5%), the miR-486 locus emerged as a significant predictor of weight loss upon low-caloric diet (LCD). Results were significant both using a single-SNP and a gene-based approach. The gene-based results were as follows:

Ottawa discovery cohort p=2.2e−5
Diogenes validation cohort p=6.61e−4
Meta-analysis of the two cohorts p=2e−6
Single-SNP results are illustrated in FIG. 1. Among 130 SNPs located nearby the miR-486 locus, 11 SNPs had p<0.0001.

Results for those 11 top SNPs are shown below in Table 1.

TABLE 1

| chr | pos | SNP rsid | Associated allele | Effect of associated allele | p.value | Shown as SEQ ID NO: |
|---|---|---|---|---|---|---|
| 8 | 41534485 | rs545936 | G | improved weight loss | 1.15E-06 | 3 |
| 8 | 41535886 | rs56306962 | C | improved weight loss | 1.25E-06 | 6 |
| 8 | 41516915 | rs6981587 | C | improved weight loss | 1.54E-06 | 4 |
| 8 | 41533847 | rs518629 | T | improved weight loss | 1.57E-06 | 7 |
| 8 | 41533201 | rs77072645 | G | improved weight loss | 1.58E-06 | 8 |
| 8 | 41532647 | rs486499 | G | improved weight loss | 1.60E-06 | 9 |
| 8 | 41535403 | rs554340 | C | improved weight loss | 1.60E-06 | 10 |
| 8 | 41533397 | rs519619 | A | improved weight loss | 1.69E-06 | 11 |
| 8 | 41503003 | rs11996576 | G | improved weight loss | 2.88E-05 | 12 |
| 8 | 41518872 | rs3736217 | G | improved weight loss | 6.51E-05 | 13 |
| 8 | 41519944 | rs6983305 | T | improved weight loss | 9.92E-05 | 14 | rs6981587 is predicted as a regulatory variant (Ensembl.org release 75). This SNP overlaps a transcription factor binding site; is located within a DNase sensitivity cluster; and is close to a promoter region. This SNP is also in strong linkage disequilibrium with the top SNP rs545936 (r-square=86.5%).

Example 2—miR-486 Levels Predict Changes in Clinical Outcomes Upon LCD and Weight Maintenance Using miR-486 levels, as quantified using miRNA Affymetrix arrays (see below section Quantification of miRNA levels), the association of baseline levels of miR-486 with clinical outcome during weight loss was determined.

Baseline miR-486 levels were significantly associated with weight- and glycemic-outcomes, both after LCD and after a weight maintenance phase.

| Clinical endpoint | Association pvalue for changes after LCD | Association pvalue for changes after weight maintenance |
|---|---|---|
| BMI (kg/m2) | 0.0191 | 0.1051 |
| Fat mass (kg) | 0.1317 | 0.0483 |
| Weight (kg) | 0.0301 | 0.1021 |
| Matsuda insulin sensitivity index | 0.0341 | 0.0212 |
| Insulinogenic index | 0.1291 | 0.0895 |
| Insulin AUC | 0.4763 | 0.0376 |
| glucose AUC | 0.0127 | 0.0051 |

These results indicated that baseline miR-486 levels are indicators of the patients' capacity to respond to a weight loss and weight maintenance intervention.

Figure 2:
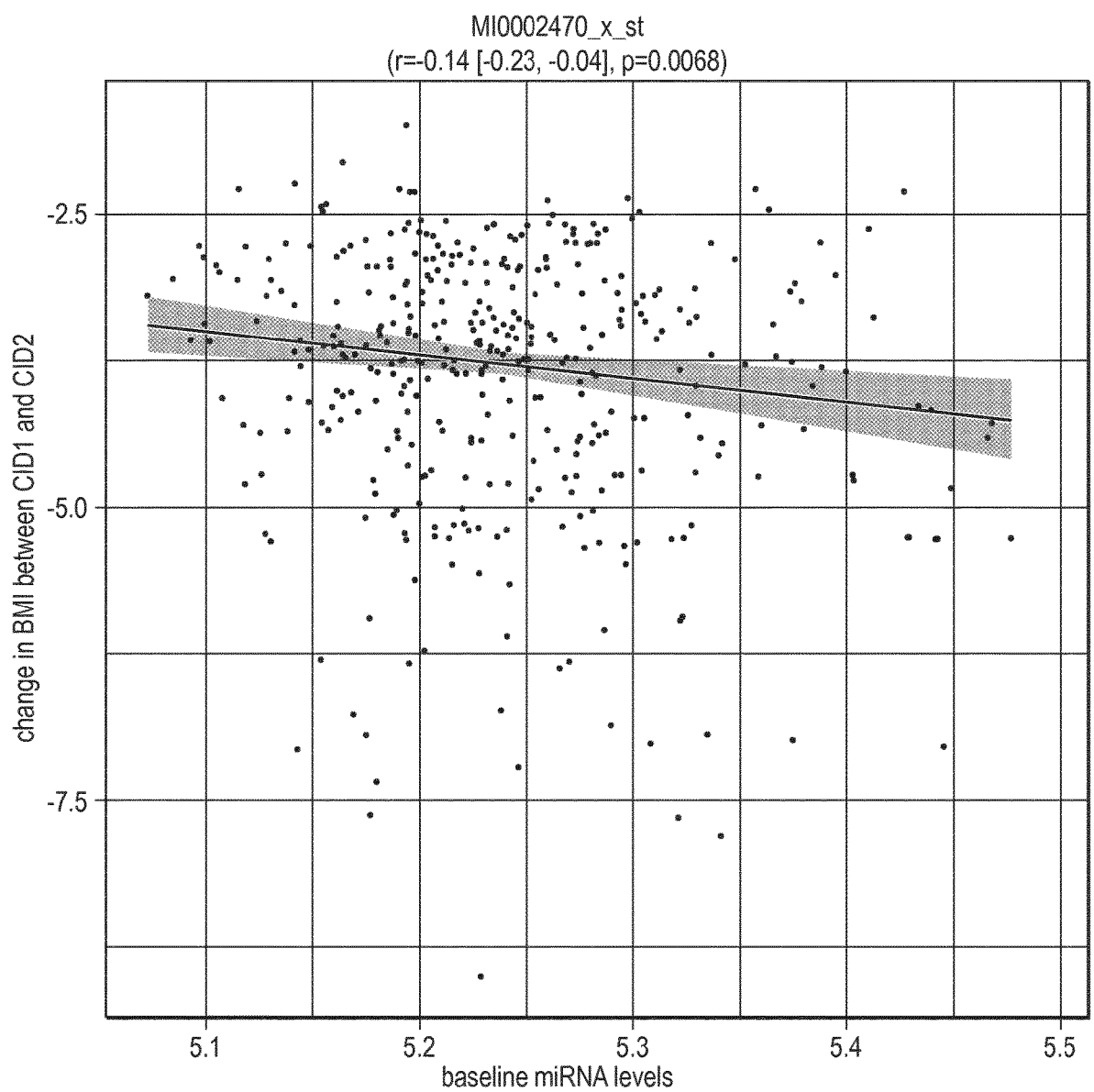
FIG. 2—Baseline miR-486 levels predict weight improvement after low-caloric diet FIG. 3—Baseline miR-486 levels predict glycemic control improvement after low-caloric diet FIG. 4—miR-486 levels predict sustained weight loss (after 6-month of weight maintenance)
Figure 3:
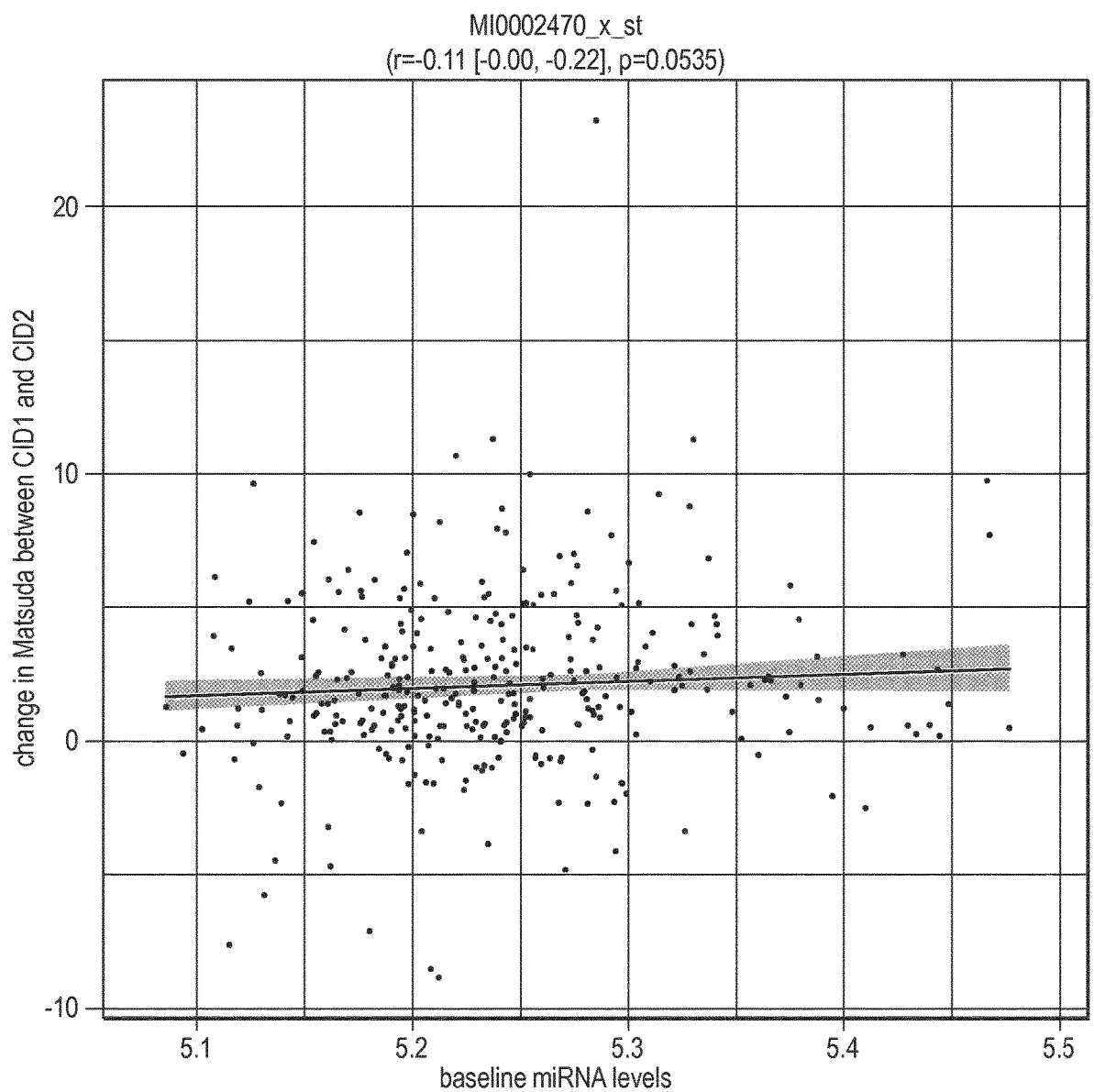
Figure 4:
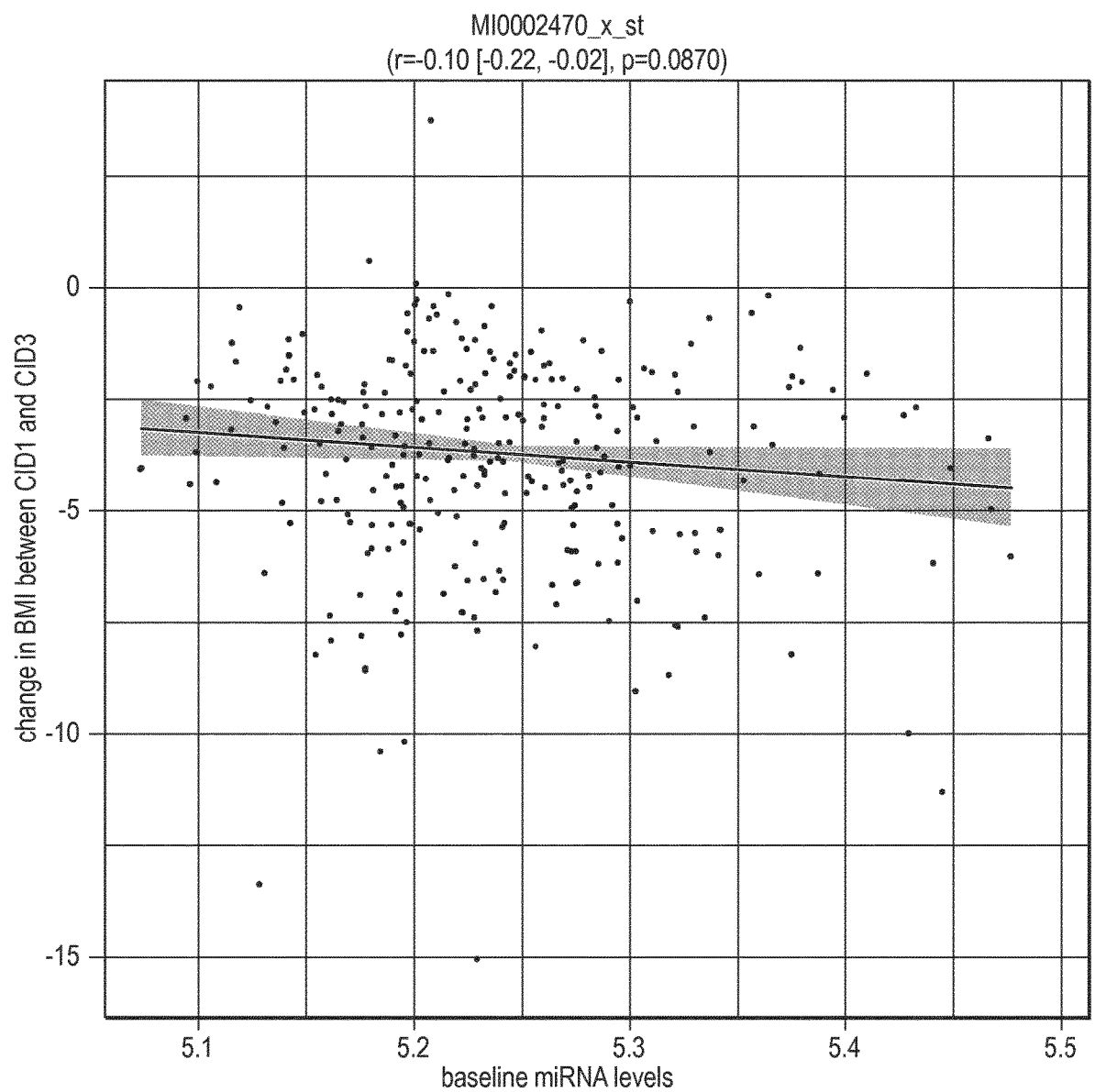
Figure 5:
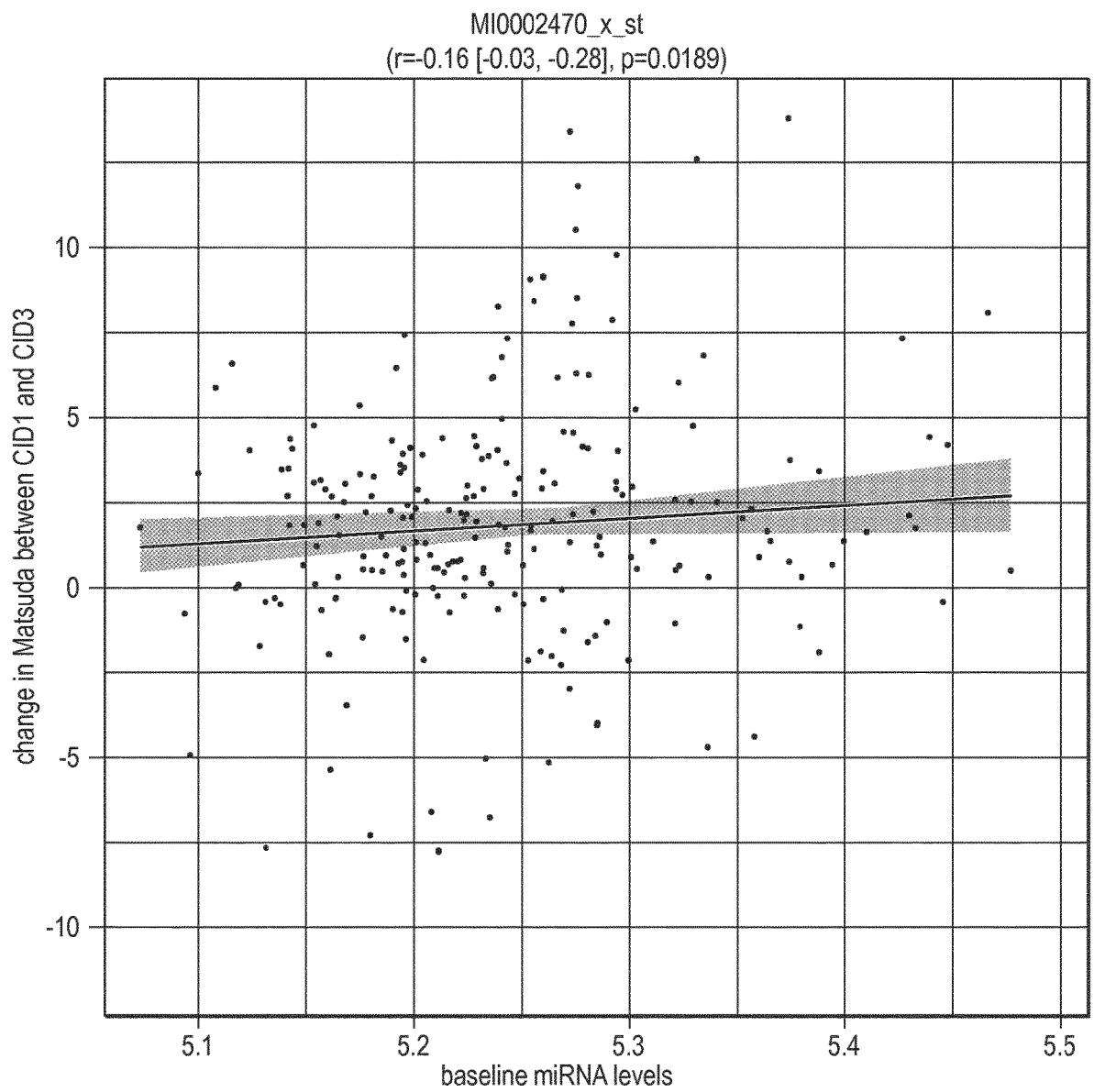
FIG. 5—Baseline miR-486 levels predict sustained glycemic control improvement (after 6-month of weight maintenance)

Specifically, high levels of miR-486 are indicators of positive clinical outcomes (i.e. improvements) upon weight loss; both for weight (see FIG. 2) and glycemic control (FIG. 3). Also, high-levels of miR-486 are predictions of clinical improvements after weight maintenance (see FIG. 4 and FIG. 5).

Example 3—miRNA SNPs Predict miRNA Levels

Figure 6:
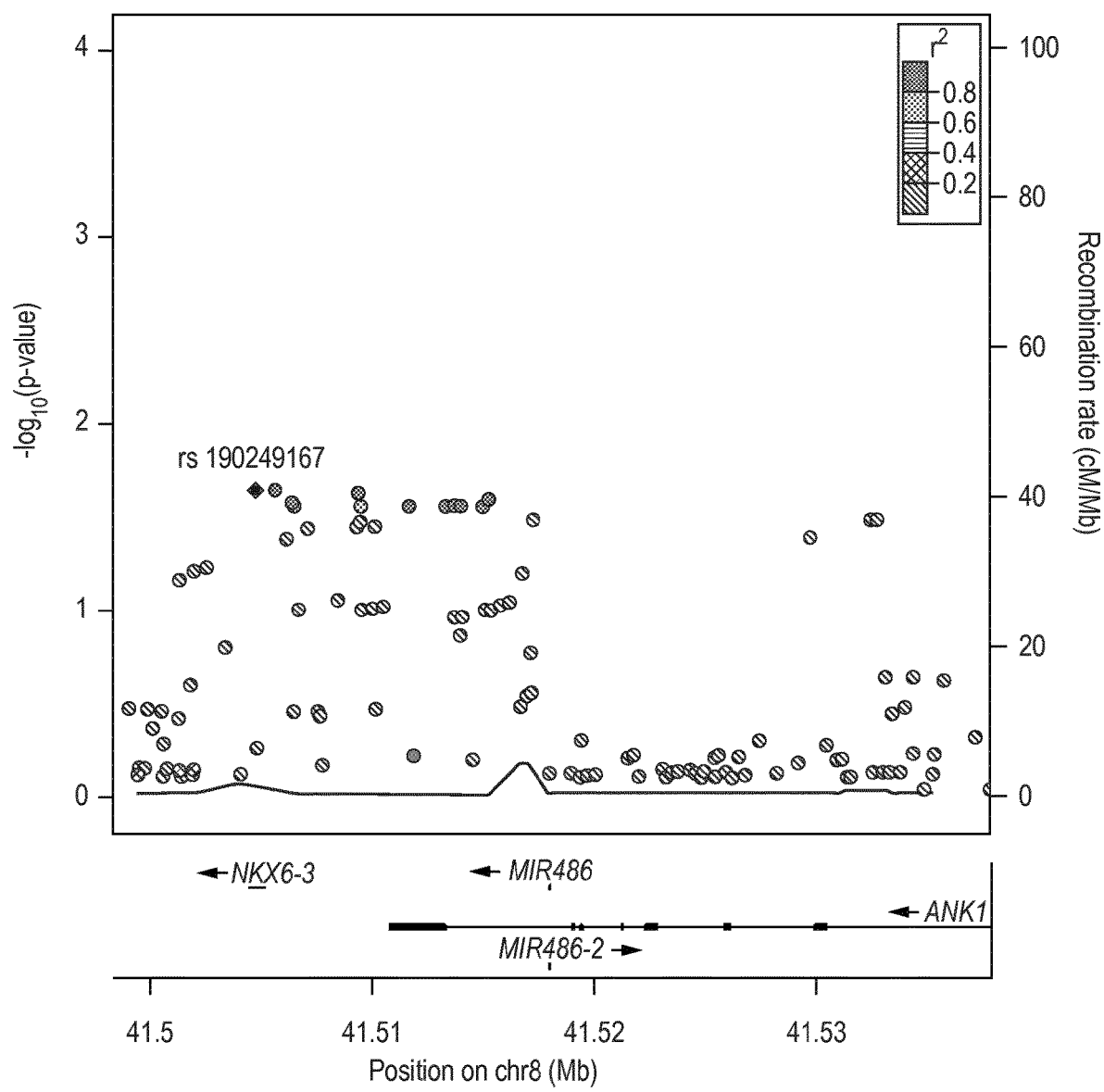
FIG. 6—SNPs near miR-486 predict mir486 expression levels

Quantitative trait analyses (QTL) identified SNPs, nearby the miR-486 gene, which were associated with miR-486 expression levels (FIG. 6). The twenty-one top SNPs (with p<5%) are listed in the table below.

TABLE 2

| chr | pos | SNP rsid | Associated allele | Effect of associated allele | p. value | Shown as SEQ ID NO: |
|---|---|---|---|---|---|---|
| 8 | 41504413 | rs190249167 | C | higher mir-levels | 0.023 | 5 |
| 8 | 41505277 | rs55794933 | A | higher mir-levels | 0.023 | 15 |
| 8 | 41509099 | rs72638941 | C | higher mir-levels | 0.024 | 16 |
| 8 | 41515015 | rs72638952 | G | higher mir-levels | 0.026 | 17 |
| 8 | 41506082 | rs72638939 | C | higher mir-levels | 0.027 | 18 |
| 8 | 41506162 | rs72638940 | A | higher mir-levels | 0.028 | 19 |
| 8 | 41509218 | rs117956059 | C | higher mir-levels | 0.028 | 20 |
| 8 | 41511410 | rs72638943 | T | higher mir-levels | 0.028 | 21 |
| 8 | 41513071 | rs72638944 | G | higher mir-levels | 0.028 | 22 |
| 8 | 41513539 | rs72638945 | C | higher mir-levels | 0.028 | 23 |
| 8 | 41513796 | rs72638947 | C | higher mir-levels | 0.028 | 24 |
| 8 | 41514758 | rs72638950 | A | higher mir-levels | 0.028 | 25 |
| 8 | 41532580 | rs78673930 | A | higher mir-levels | 0.033 | 26 |
| 8 | 41532834 | rs139183594 | T | higher mir-levels | 0.033 | 27 |
| 8 | 41509180 | rs77385495 | T | higher mir-levels | 0.034 | 28 |
| 8 | 41509083 | rs117135799 | T | higher mir-levels | 0.036 | 29 |
| 8 | 41509867 | rs117308321 | A | higher mir-levels | 0.036 | 30 |
| 8 | 41506770 | rs76356889 | T | higher mir-levels | 0.037 | 31 |
| 8 | 41529789 | rs80105613 | T | higher mir-levels | 0.041 | 32 |
| 8 | 41505849 | rs116964396 | A | higher mir-levels | 0.042 | 33 |

Therefore expression levels of miR-486 are partially regulated by nearby genetic markers.

Materials and Methods

Cohort Descriptions

Diogenes—

The Diogenes study (clinical trial.gov NCT00390637) is an interventional, multi-center pan-European study (Larsen, T. M. et al.; *N. Engl. J. Med.* 363, 2102-2113 (2010) & *Obes. Rev. Off. J. Int. Assoc. Study Obes.* 11, 76-91 (2010)). Eight partners participated to the study: Bulgaria, Czech republic, Denmark, Germany, Greece, Netherlands, Spain and United Kingdom. Participants followed an 8-weeks low-caloric diet using Modifast® (at 800 kcal/day). Participants that lost at least 8% of initial weight were randomly assigned to one of the five maintenance diets for 6-months or 12-months for subjects from Denmark and Netherlands. A total of 1209 adults were screened (mean age, 41 years; body-mass index 34 kg/m$^2$), of whom 938 entered the low-calorie-diet phase of the study. A total of 773 participants who completed that phase and that lost at least 8% of initial weight were randomly assigned to one of the five maintenance diets; 548 completed the intervention.

Ottawa—

This cohort includes 2383 overweight and obese patients of the Weight Management Clinical of The Ottawa Hospital who underwent a meal replacement program diet combined with an exercise regime to reduce weight during 6 to 12 weeks using Optifast®, and were monitored for up to 36 weeks, checking their weight, height, blood pressure, at every visit, and at week 1, they had a range of biochemistry measurements performed, from lipids profile to fasting insulin and blood glucose. After exclusion criteria were applied, 2032 patients remained: 1448 females and 584 males.

Quantification of miRNA Levels

Quantification of miRNA levels from adipose tissue biopsies was performed using the Affymetrix Gene Chip miRNA 4.0 array (http://www.affymetrix.com). Experiments were performed according to the manufacturer's protocol.

Clinical Data Analyses

Association between a clinical outcome and baseline miRNA levels was tested using linear effect model. Baseline miRNA levels, gender and age were modelled as fixed effects; while the country (centre) was modelled as a random effect.

Genotyping

Subjects were genotyped on Illumina Human Core arrays (www.illumina.com) following the manufacturer's recommendations. SNPs exhibiting either low call rate (<95%), violating Hardy-Weinberg equilibrium (FDR<20%), minor allele frequency <0.2% were discarded. Imputation of additional genetics markers was performed using the latest version of the 1000 Genome Project. Post-processing removed SNPs with INFO score below 0.8 or allele frequency below 1%. Subjects with low call rate (<95%), gender discrepancies compared to clinical records, abnormal autosomal heterozygosity, or close-family members (identify-by-state >95%) were discarded. Upon quality control, data were available for 698 Diogenes subjects and 1166 Ottawa subjects; both cohort having genotype data for nearly 5 million markers. This demonstrates that a comprehensive assessment was made of common markers (i.e. frequent SNPs, with frequency greater than 1%).

Genetics Data Analyses

Single-SNP GWAs were performed using linear mixed effect models to adjust for population stratification (Yang et al.; Nat. Genet. 46, 100-106 (2014)). Adjustment was performed using the "leave-one-chromosome out" approach. Gene-based analyses were performed using VEGAS (Mishra et al; win Res. Hum. Genet. Off J. Int. Soc. Twin Stud. 18, 86-91 (2015)) using LD patterns from European ancestry population from the 1000 Genome project, with a gene-block size of 20 Kb and considering the top 80% SNPs for analysis. The phenotype (change in BMI during LCD) was adjusted for subjects' gender and age. Single-SNP and gene-based analyses were performed separately for the two cohorts (Diogenes and Ottawa). Single-SNP and gene-based results from the two cohorts were subsequently meta-analyzed using GWAMA (Migi et al; BMC Bioinformatics 11, 288 (2010)) using random-effect modeling and double genomic-control correction. For gene-based analyses, adjustment for multiple-testing was performed using Benjamini-Hochberg correction (Benjamin et al; J. R. Stat. Soc. Ser. B Methodol. 57, 289-300 (1995)).

Quantitative Trait Analyses

Analyses were performed using data from the DiOGenes cohort (more than 5M genetic markers and miR-486 baseline levels as quantified from the Affymetrix Gene Chip). Association was tested at the single-SNP level using linear mixed effect model (Yang et al; as above). The phenotype (miR-486 levels at CID1) was adjusted for subjects' gender and age.

The invention claimed is:

1. A method for weight loss in a human, the method comprising:
   (a) determining a presence of Guanine (G) at position 26 of SEQ ID NO: 3 (rs545936) of the human; and
   (b) administering a dietary intervention to the human having a G at position 26 of SEQ ID NO: 3 (rs545936), wherein the dietary intervention comprises a low calorie diet comprising a calorie intake of 600-1200 kcal/day for a duration of 4 weeks to 16 weeks.

2. The method according to claim 1, wherein the method further comprises determining one or more anthropometric measures and/or lifestyle characteristics of the subject.

3. A method for improvement in glycemic control in a human, the method comprising:
   (a) determining a presence of Guanine (G) at position 26 of SEQ ID NO: 3 (rs545936) of the human; and
   (b) administering a dietary intervention to the human having a G at position 26 of SEQ ID NO: 3 (rs545936), wherein the dietary intervention comprises a low calorie diet comprising a calorie intake of 600-1200 kcal/day for a duration of 4 weeks to 16 weeks.

* * * * *